(12) United States Patent
Lim

(10) Patent No.: US 7,954,181 B2
(45) Date of Patent: Jun. 7, 2011

(54) BIDET HAVING ENEMA FUNCTION

(75) Inventor: Young Kyun Lim, Incheon (KR)

(73) Assignee: Izen Co., Ltd. (KR)

( * ) Notice: Subject to any disclaimer, the term of this patent is extended or adjusted under 35 U.S.C. 154(b) by 1182 days.

(21) Appl. No.: 11/632,073

(22) PCT Filed: Nov. 26, 2004

(86) PCT No.: PCT/KR2004/003085
§ 371 (c)(1),
(2), (4) Date: Jan. 10, 2007

(87) PCT Pub. No.: WO2006/006756
PCT Pub. Date: Jan. 19, 2006

(65) Prior Publication Data
US 2008/0047055 A1      Feb. 28, 2008

(30) Foreign Application Priority Data

Jul. 12, 2004    (KR) .................. 10-2004-0053840
Oct. 22, 2004   (KR) .................. 20-2004-0029917 U
Oct. 25, 2004   (KR) .................. 10-2004-0085322

(51) Int. Cl.
*E03D 11/00*    (2006.01)
(52) U.S. Cl. ............................................. 4/420
(58) Field of Classification Search .......... 4/420.4, 4/443, 447; 239/590
See application file for complete search history.

(56) References Cited

U.S. PATENT DOCUMENTS 1,886,623 A * 11/1932 Barnes .................. 239/590 X
6,754,912 B1 * 6/2004 Hayashi et al. ........... 4/420.4 X

FOREIGN PATENT DOCUMENTS

| JP | 04-146341 | 5/1992 |
| JP | 07-042216 | 2/1995 |
| JP | 08-199656 | 8/1996 |
| JP | 09-316968 | 12/1997 |
| JP | 2000-160649 | 6/2000 |
| JP | 2001-140323 | 5/2001 |
| JP | 2002-155565 | 5/2002 |
| JP | 2002-194796 | 7/2002 |
| JP | 2002-294817 | 10/2002 |
| KR | 20-0363500 | 9/2004 |

* cited by examiner

*Primary Examiner* — Lori Baker
(74) *Attorney, Agent, or Firm* — Cantor Colburn LLP

(57) ABSTRACT

Disclosed herein is a multi-functional bidet having an extra function such as an enema function for a constipated person, in addition to its normal function of cleansing pubic area and anal region. Specifically, the bidet of the invention is constructed such in a manner that an anus-cleansing function, a bidet cleansing function, and an enema function are embodied in a single nozzle; or any one function is constituted on a spray tip projected from the separate spray nozzle body; or one or two functions among the anus-cleansing function, the bidet cleansing function and the enema function are embodied in two or three spray nozzles, which are projectably inserted in the lower central portion of the bidet body so as to be arranged horizontally adjacent to one anther; or one or two functions among the anus-cleansing function, the bidet cleansing function and the enema function are embodied in two or three spray nozzles, which are projectably inserted in the lower central portion of the bidet body so as to be arranged vertically adjacent to one anther.

6 Claims, 22 Drawing Sheets

BIDET HAVING ENEMA FUNCTION

CROSS REFERENCE TO RELATED APPLICATION

This application is the National Phase application of International Application No. PCT/KR2004/003085, filed Nov. 26, 2004, which designates the United States and was published in English. This application, in its entirety, is incorporated herein by reference

TECHNICAL FIELD

The present invention relates to a bidet having additional functions. Particularly, the invention relates to a multi-functional bidet, in which an enema function is provided, along with its normal functions of cleansing the anal or pubic region of the human body, thereby enabling a pleasant relief, in particular, of a constipated person.

BACKGROUND ART

A bidet is used for washing the genital and anal areas using cleaning water of appropriate temperature sprayed from the center of the bidet, instead of a toilet paper after relief stool.

Although such a bidet has been developed originally for washing the pubic area for females, now it is popular among people of all ages and both sexes, since it is known to be more hygienic to wash the anus with water instead of paper after relief. Cleansing the pubic/anal regions with water avoids germ infection, and is very useful for preventing hemorrhoids and other anal disease. In addition, it is very effective for women with gynecology diseases. It is also very useful for the elderly or obese people to relieve themselves with great convenience.

As shown in FIG. 1, such a bidet is composed of a bidet body 2001 rested on top of a toilet bowl and having a water container for storing filtered tap water, a bidet/cleansing nozzle (or an anus-cleansing nozzle) 2002 for spraying the stored cleansing water to the pubic area or anal region according to a user's selection, a toilet seat 2003 for a user to sit on for relief, and a control panel 2004 for controlling the bidet's functions depending on situations.

With the bidet having the above-described construction, after a user sits on the toilet seat 2003 and relives himself or herself, he or she selects and presses either a bidet cleansing button or an anal cleaning button. Then, by the water pressure of the cleansing water stored in the water container of the body 2001, the selected bidet-cleansing nozzle (or anus nozzle) 2002 is projected with a certain distance while pressurizing a restoring spring (not shown). Thereafter, the cleansing water is sprayed with a pressure suitable to the selected function to thereby cleanse the pubic area or anus, which is then dried with a warm air, thereby carrying out the pubic/anal area cleansing work.

Recently, many additional functions have been added to the original functions of the bidets and thus its use has been widely extended. For example, it includes a massaging function bidet with a massage mode, in which the spray pressure of warm water is controlled; an infrared emitting function bidet with an infrared light emitter inside the toilet bowl; an aroma pack inserted nozzle tip used for reducing bad smell or inflammation treatment; a bidet with an electrolytic water generator to sterilize water without chemical treatments; and a bidet having an alarm for ringing the alarm in case where the relieving time is unusually extended.

However, these previous attempts including the massaging, the infrared emitting, the aroma pack, and the showering function are not directly directed to the core function of a bidet, but simply added to the common bidets. In fact, they are not the attempts to improve the convenience of relief or the users' hygienic.

Among them, the electrolytic water generator and the relieving time control alarm approaches can be considered as attempts in order to prevent genital and anal areas infections by using the electrolytic water as a cleansing water and reducing the relieving time. However, it makes the system more complicated because extra additional electrolytic water generator, timer and alarm devices are needed. Also, these approaches are not directly related to the solutions to the problems concerning the relief, such as constipation.

Accordingly, there is need to provide a multi-functional bidet, which does not need any additional equipment, while directly improving user's sanitary concerns such as constipation.

DISCLOSURE OF INVENTION

The present invention has been made to solve the above problems in the art, and it is an object of the invention to provide a multi-functional bidet is provided, which can improve convenience of relief and sanitary concerns, called a core function of the bidet, and thus the user's health, without necessity of complicating the bidet structure or increasing the cost thereof owing to addition of other separate equipment.

In order to accomplish the above object, according to one aspect of the invention, there is provided a bidet having an enema function. The bidet of the invention comprises: a) a support mounted on the bottom face of a bidet body; b) a controller mounted on aside of the bidet body and for selecting an anus-cleaning function, a bidet-cleaning function, and an enema function, and interrupting a selected function; c) an operator attached to an end portion of the support and for moving a three-directional nozzle correspondingly so as to perform the function selected by the controller; d) a waterway converter for converting a waterway in order for a cleansing water to be supplied according to the function selected in the controller; and e) a spray-nozzle structure having the three-directional nozzle, wherein the three-directional nozzle is moved to a sliding space of the support and sprays the cleansing water passed through the waterway convert, thereby carrying out the function selected in the controller.

Preferably, the support comprises: a) the sliding space where the three-directional nozzle slides thereon, the sliding space being mounted slantedly on the bottom face of the bidet body; b) a guidance space provided at the other end portion of the sliding space and for preventing escape of the three-directional nozzle sliding on the sliding space; and c) a support plate integrally provided and having a support hole fluid-communicatively formed vertically to an end portion of the sliding space.

Preferably, the operator comprises: a) an operating motor affixed to one side of the support plate such that a rotating axle is projected in the support hole of the support, the operating motor being clockwise or counterclockwise rotated in order for the three-directional nozzle to be located correspondingly to the function selected in the controller; and b) a take-up member combined with the rotating axle of the operating motor and being rotated in the same manner of the operating motor; wherein an accommodating member affixed to the other side of the support plate receives the take-up member so as to prevent a leaf spring wound around the take-up member from escaping.

In addition, preferably, the waterway converter comprises: a) a stepping motor having a rotating axle projected therefrom, the rotating axle being clockwise or counterclockwise rotated so as to supply a cleaning water to the function selected in the controller; b) a connection member connected to the rotating axle of the stepping motor and being rotated in the same manner as the stepping motor; c) a fixed member mounted on one side of the stepping motor and receiving the connection member such that the end portion of the connection member is projected; d) a guidance member connected to a projected portion from the fixed member in order for the connection member to be freely rotated, the guidance member having a cleansing guide hole, a bidet guide hole, and an enema guide hole fluid-communicatively formed in the inner side thereof; e) a conversion member connected to an end portion of the connection member and closely contacted with the guidance member, the conversion member having a cleansing drain hole, a bidet drain hole, and an enema drain hole fluid-communicatively formed such that the direction of the cleaning water is fluid-communicated respectively with the cleansing guide hole, the bidet guide hole, and the enema guide hole of the guidance member according to the rotation of the stepping motor; f) a support member for receiving the guidance member mounted on the connection member and the conversion member in the inside of a body such that the outer circumferential face of the guidance member is tightly contacted with the inner circumferential face of the body, the body having an inlet hole projected on the outer circumferential face thereof for in-flowing the cleaning water, a moving hole being fluid-communicatively formed in a side face of the body so as to be fluid-communicated respectively with the cleansing drain hole, the bidet drain hole, and the enema drain hole; and g) a packing mounted on the outer circumferential face of the moving hole of the support member.

Furthermore, the guidance member may be constructed in such a manner that the bidet guide hole is fluid-communicatively formed at the position perpendicularly crossing the center of the cleansing guide hole fluid-communicatively formed in the upper portion of the guidance member, and the enema guide hole is fluid-communicatively formed at the position facing the cleansing guide hole.

The conversion member may preferably be constructed in such a manner that the cleansing drain hole and the enema drain hole are fluid-communicatively formed between the cleansing guide hole and the enema guide hole, and the bidet drain hole is fluid-communicatively formed between the bidet guide hole and the enema guide hole.

The three-directional nozzle may comprise: a) a cleansing water moving pipe connected to an end portion of the support member so as to receiving the packing of the waterway converter, the cleansing water moving pipe having a cleansing moving hole, a bidet moving hole, and an enema moving hole fluid-communicatively formed so as to lie in the same line as the cleansing guide hole, the bidet guide hole, and the enema guide hole; and a spraying cap connected to an end portion of the cleansing water moving pipe and having a cleansing spraying hole, a bidet spraying hole, and an enema spraying hole fluid-communicatively formed so as to be fluid-communicated with the cleansing moving hole, the bidet moving hole, and the enema moving hole.

According to another aspect of the invention, there is provided a bidet having an enema function. The bidet of the invention comprises: a bidet body rested on the upper portion of a toilet bowl and having a water container for storing cleansing water filtered from tap-water, a toilet seat for a user to be seated to reliever himself or herself, a controller for controlling the function of bidet depending on the user's need, and a spraying nozzle member for spraying the stored cleansing water into the user's pubic area or anus area depending on the user's selection; wherein the spraying nozzle member includes a spray nozzle body having two spray holes fluid-communicated therewith, the two spray holes being selected from a cleansing hole for spraying a cleansing water for anus cleaning, a bidet hole for spraying a cleansing water for pubic-area cleaning, and an enema hole for spraying an enema water, and a spray tip is projectably inserted in one side of the leading edge of the spray nozzle body, the spray tip being fluid-communicated with the unselected spray hole from the cleansing hole, the bidet hole, and the enema hole.

Preferably, the spray hole fluid-communicated with the spray nozzle body is a single spray hole configured so as to perform two functions by spraying the cleansing water in different pressures and directions.

According to yet another aspect of the invention, there is provided a bidet having an enema function. The bidet of the invention comprises: a bidet body rested on the upper portion of a toilet bowl and having a water container for storing cleansing water filtered from tap-water, a toilet seat for a user to be seated to reliever himself or herself, a controller for controlling the function of bidet depending on the user's need, and a spraying nozzle member for spraying the stored cleansing water into the user's pubic area or anus area depending on the user's selection; wherein the spraying nozzle member is constructed in such a way that two or three spay nozzles are projectably inserted in the lower portion of the center of the bidet body and arranged horizontally so as to be placed adjacent to one another, each spray nozzle having one or two spray holes fluid-communicated therewith, the spay holes being selected from a cleansing hole for spraying a cleansing water for anus cleaning, a bidet hole for spraying a cleansing water for pubic-area cleaning, and an enema hole for spraying an enema water.

According to further aspect of the invention, there is provided a bidet having an enema function. The bidet of the invention comprises: a bidet body rested on the upper portion of a toilet bowl and having a water container for storing cleansing water filtered from tap-water, a toilet seat for a user to be seated to reliever himself or herself, a controller for controlling the function of bidet depending on the user's need, and a spraying nozzle member for spraying the stored cleansing water into the user's pubic area or anus area depending on the user's selection; wherein the spraying nozzle member is constructed in such a way that two or three spay nozzles are projectably inserted in the lower portion of the center of the bidet body and arranged vertically so as to be placed adjacent to one another, each spray nozzle having one or two spray holes fluid-communicated therewith, the spay holes being selected from a cleansing hole for spraying a cleansing water for anus cleaning, a bidet hole for spraying a cleansing water for pubic-area cleaning, and an enema hole for spraying an enema water.

In case where two spray nozzles are comprised, preferably the spray hole included in the spay nozzle having two spray holes is a single spray hole configured so as to perform two functions by spraying the cleansing water in different pressures and directions.

According to further aspect of the invention, there is provided a spray nozzle structure for a bidet having an enema function. The spray nozzle structure comprises a spray cap having an enema hole for carrying out an enema function, wherein a guide groove is formed projectedly downwardly from the upper portion of an enema spray hole so as to prevent turbulence of a cleansing water passing through the discharge hole formed inside the enema spray hole of the spray cap, and the spray nozzle structure comprises a cleansing water guide rib having a guide hole fluid-communicatively formed in a straight line inside the guide groove, the guide hole guiding the cleansing water discharged with a pressure such in a way as to stimulate an anus.

Preferably, the guide hole may have the same area as the discharge hole formed inside the spray hole.

According to all the embodiments of the present invention, the inventive bidet includes essential constitutional elements such as a bidet body rested on the upper portion of a toilet bowl and having a water container for storing cleansing water filtered from tap-water, a toilet seat for a user to be seated to reliever himself or herself, a controller for controlling the function of bidet depending on the user's need, and a spraying nozzle member for spraying the stored cleansing water into the user's pubic area or anus area depending on the user's selection, the spraying nozzle member being an specific applicable object of the present invention. The present invention can be also implemented by various configurations including a double spraying nozzle member structure having an enema function applied thereto.

BRIEF DESCRIPTION OF DRAWINGS

Further objects and advantages of the invention can be more fully understood from the following detailed description taken in conjunction with the accompanying drawings, in which:

FIG. 6 shows the operational state of an anal cleaning mode of the first embodiment, where

FIG. 7 shows an operation of a bidet cleansing mode of the first embodiment, where

FIG. 8 shows an operation of an enema mode of the first embodiment, where

BEST MODE FOR CARRYING OUT THE INVENTION

The preferred embodiments of the invention will be explained in detail with reference to the accompanying drawings.

Figure 1:
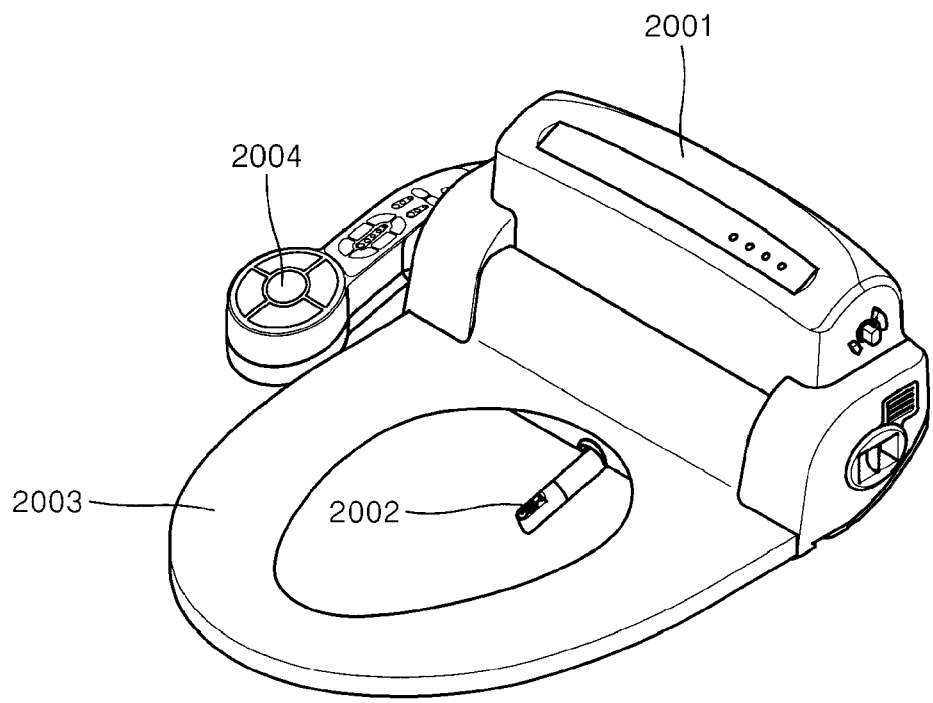
FIG. 1 is a perspective view showing the structure of a conventional bidet.
Figure 2A:
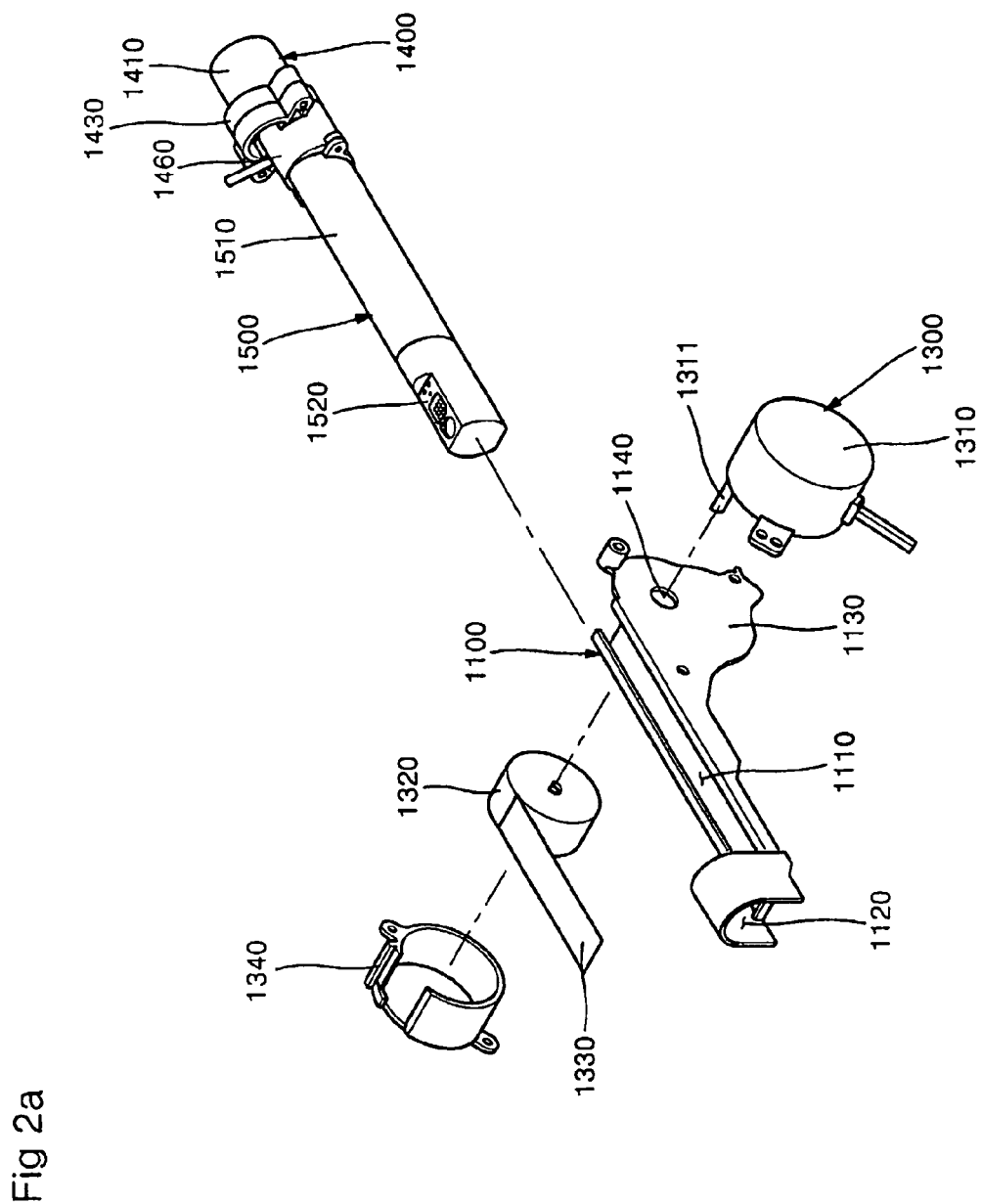
FIG. 2a and FIG. 2b are an exploded perspective view of a first embodiment of the invention.
Figure 2B:
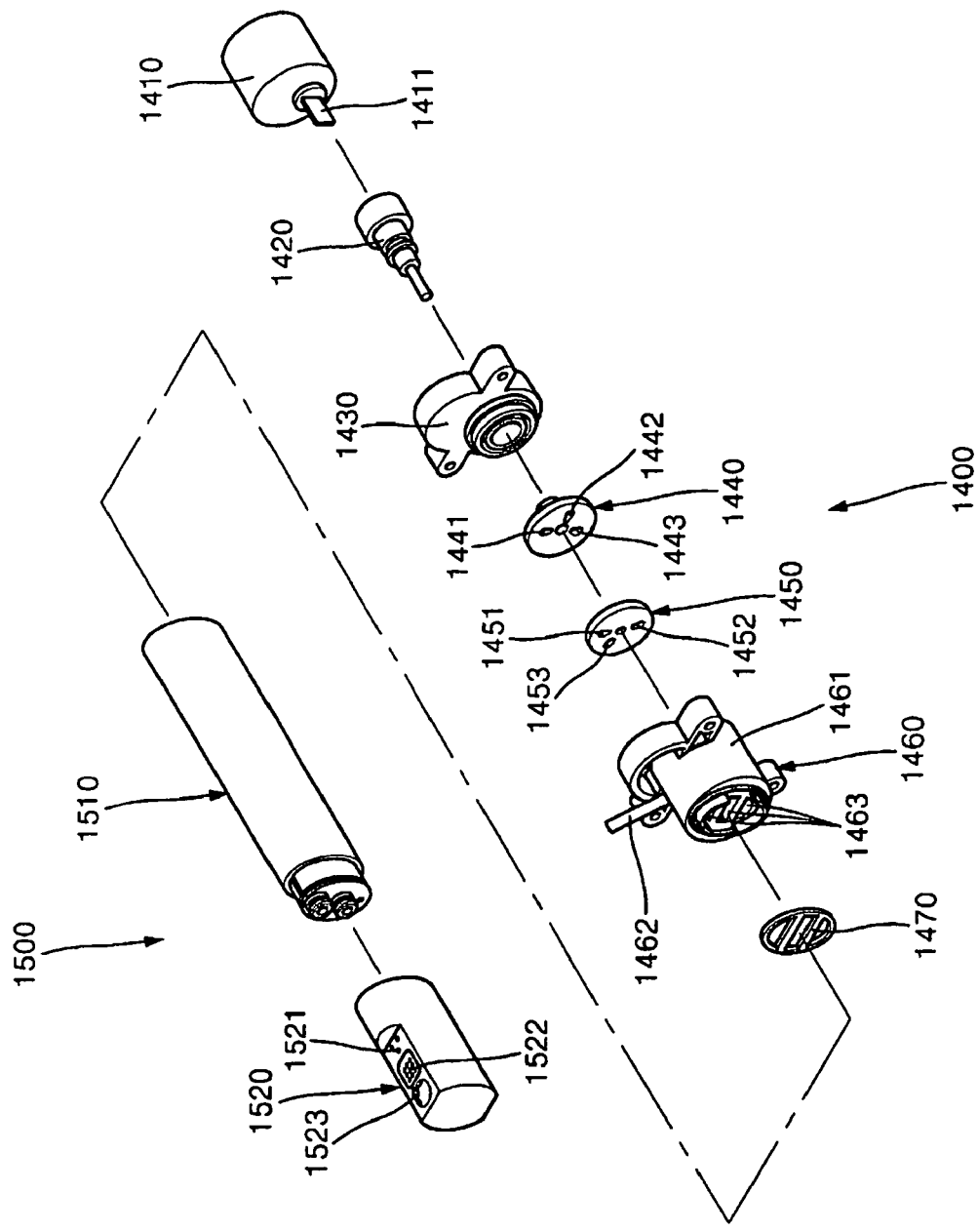
Figure 3:
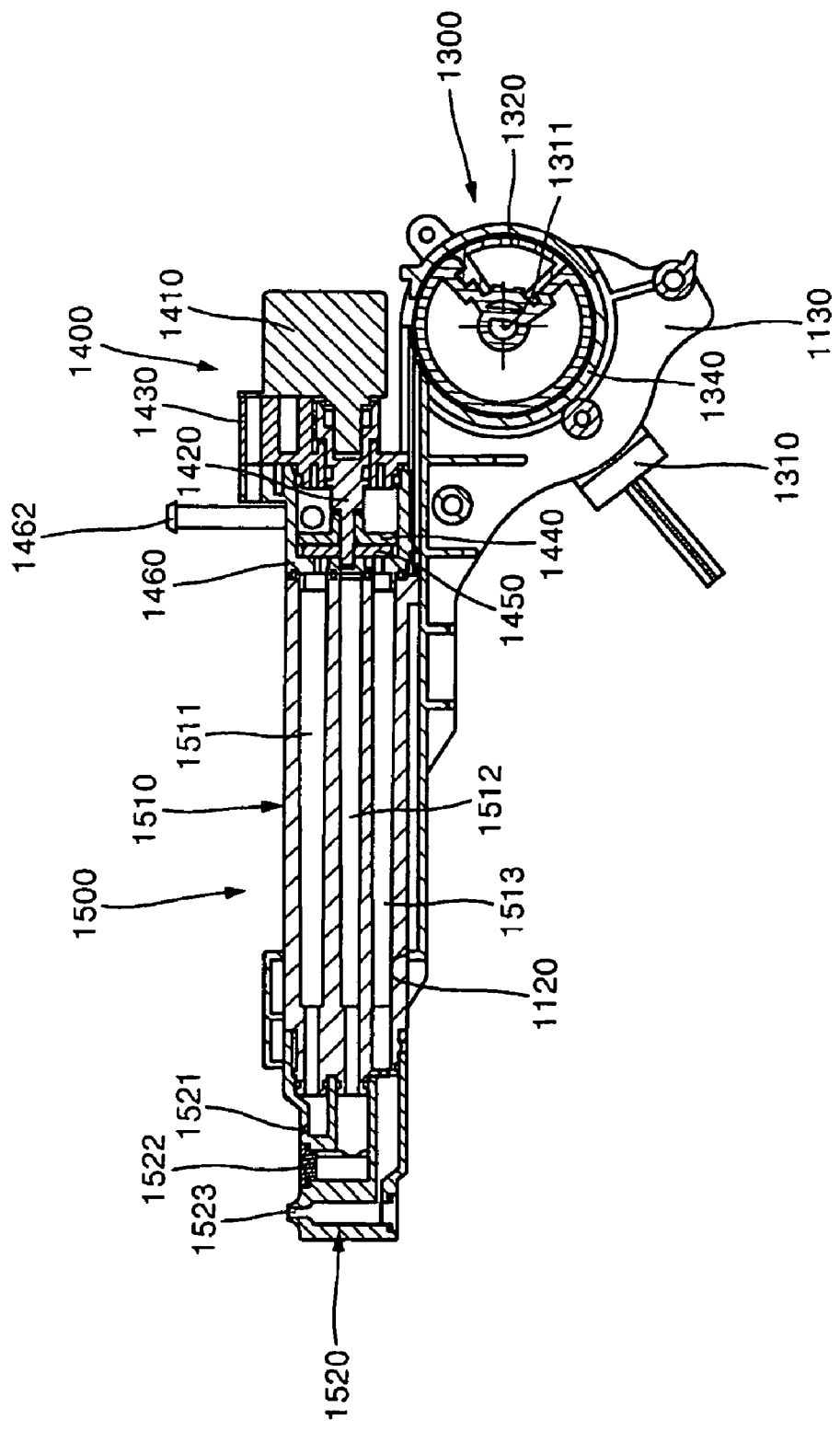
FIG. 3 is a cross-sectional side view of the first embodiment of the invention when assembled.
Figure 4:
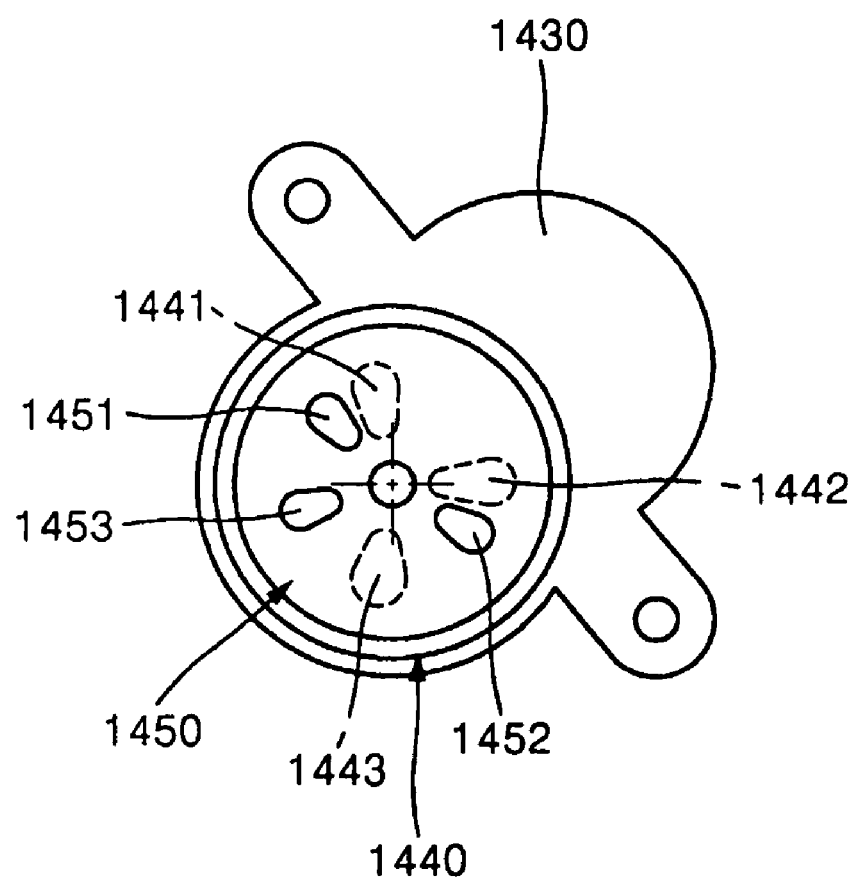
FIG. 4 is a cross-sectional front view of the first embodiment of the invention when assembled.
Figure 5:
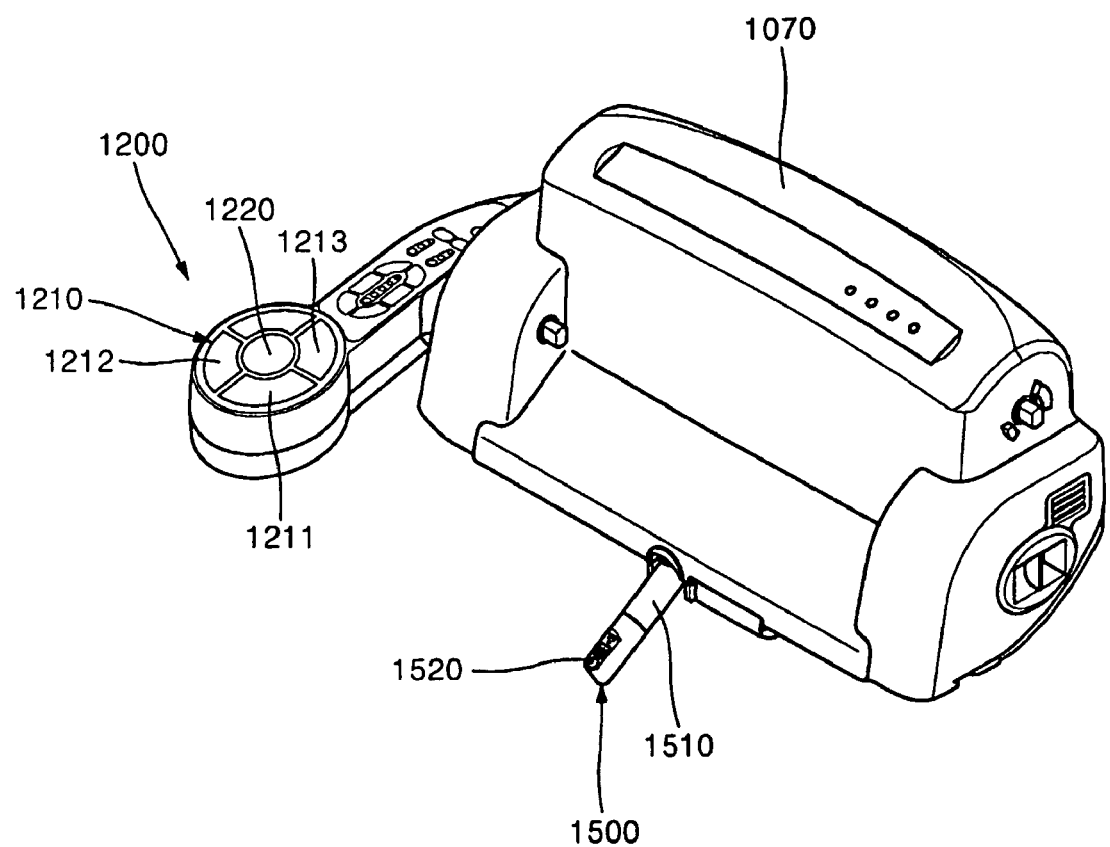
FIG. 5 is a perspective view of the first embodiment of the invention when installed.
Figure 6A:
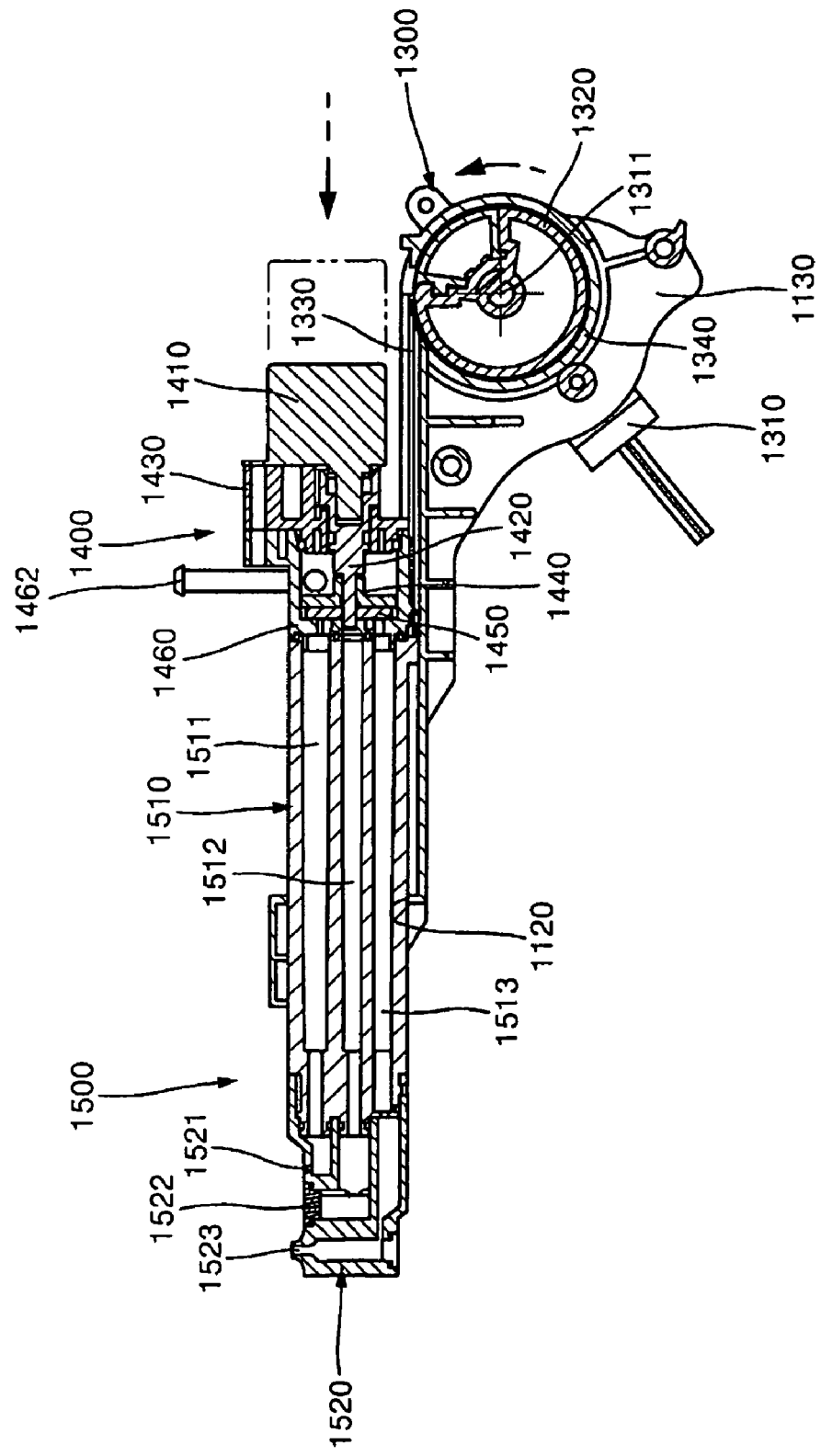
FIG. 6a shows the movement of the nozzle in the support so as to cleanse anal region.
Figure 6B:
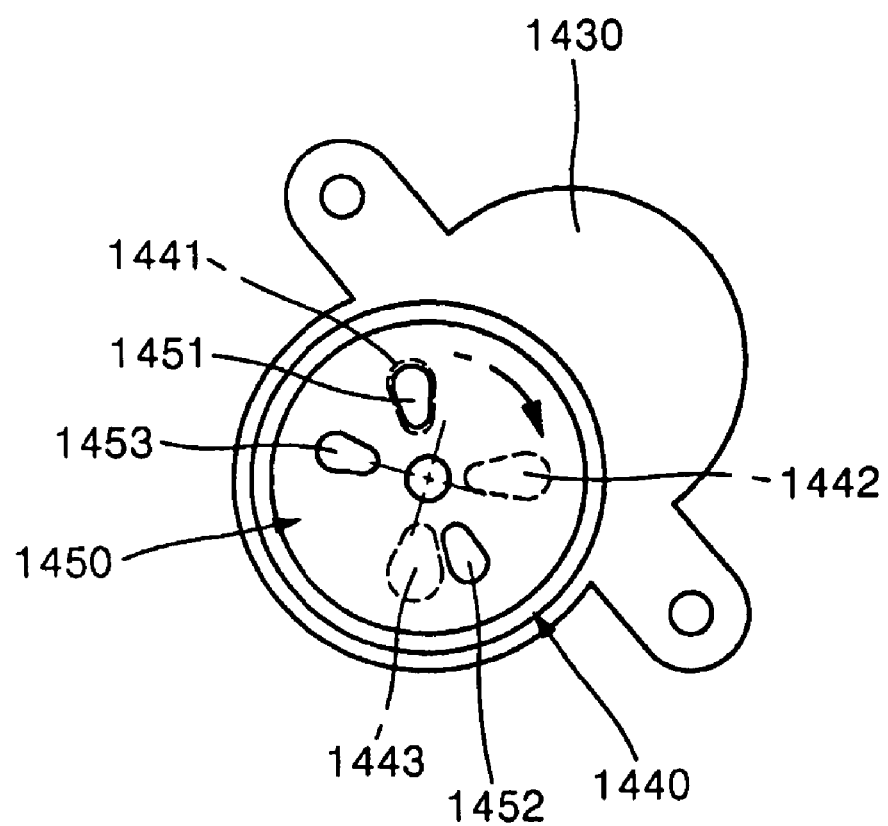
FIG. 6b is a cross-sectional view of the waterway converter.
Figure 6C:
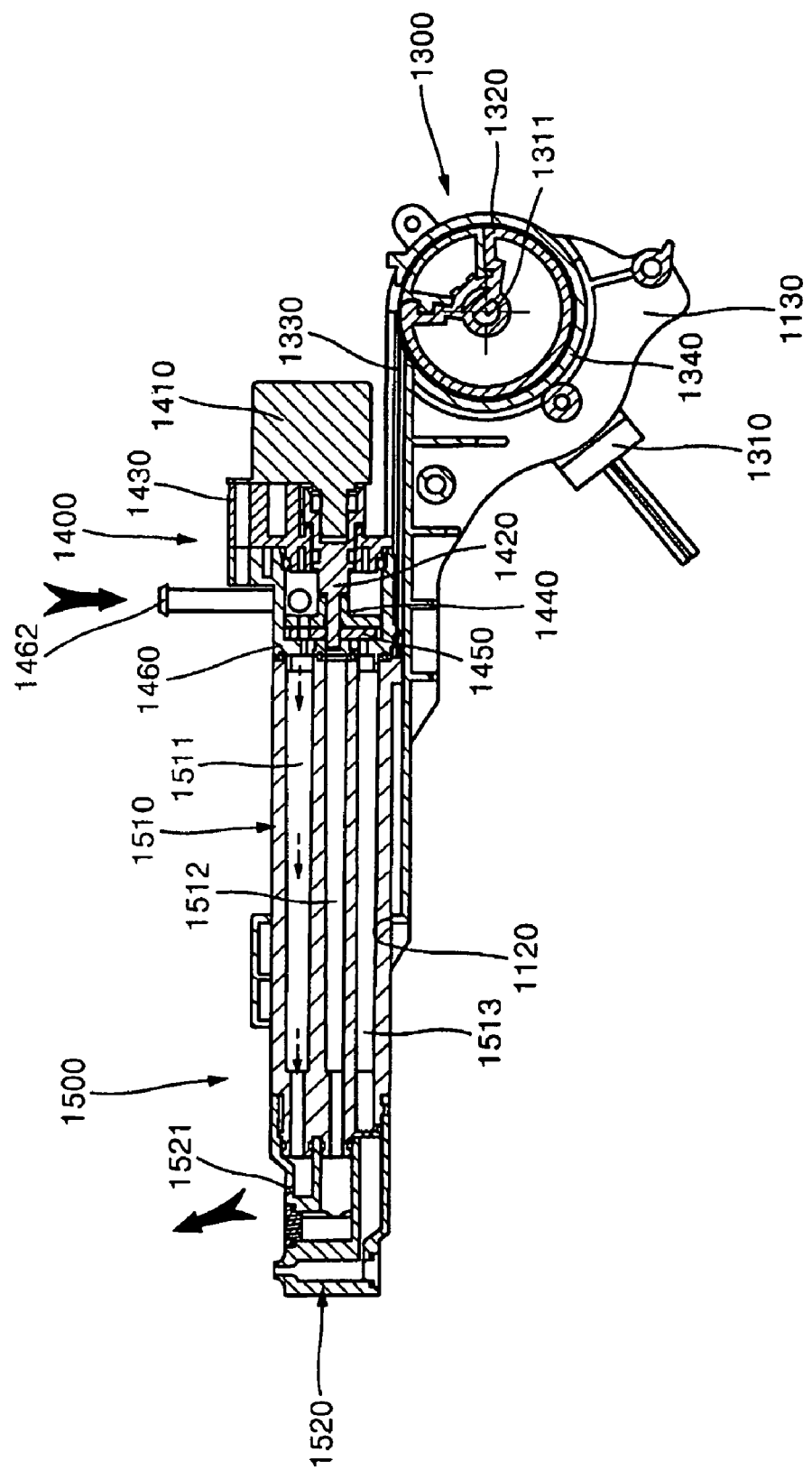
FIG. 6c is a cross-sectional view of the waterway converter where the cleansing water passed through the waterway converter is sprayed to the spray cap.
Figure 7A:
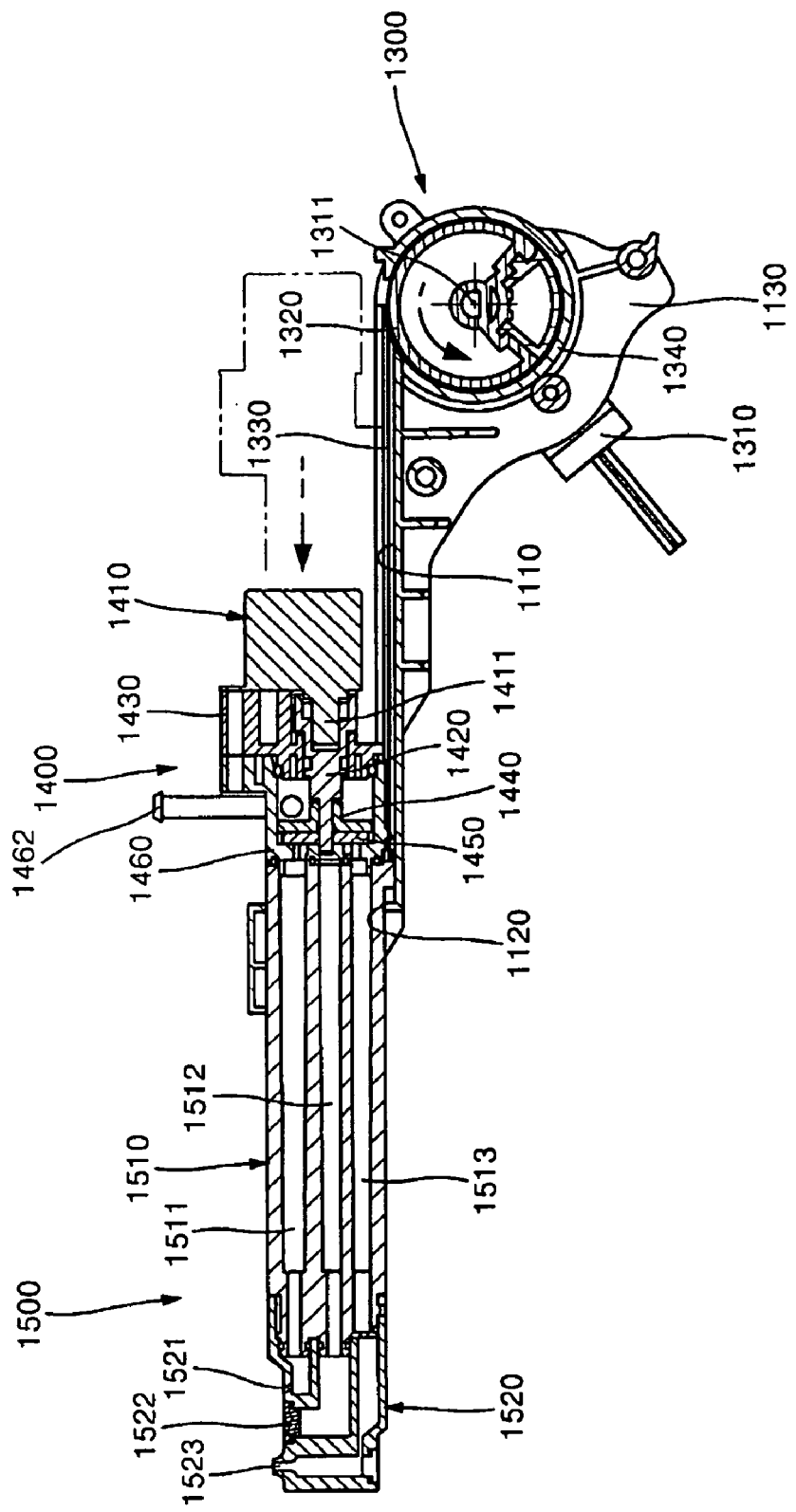
FIG. 7a shows the movement of the nozzle in the support for carrying out the bidet cleansing.
Figure 7B:
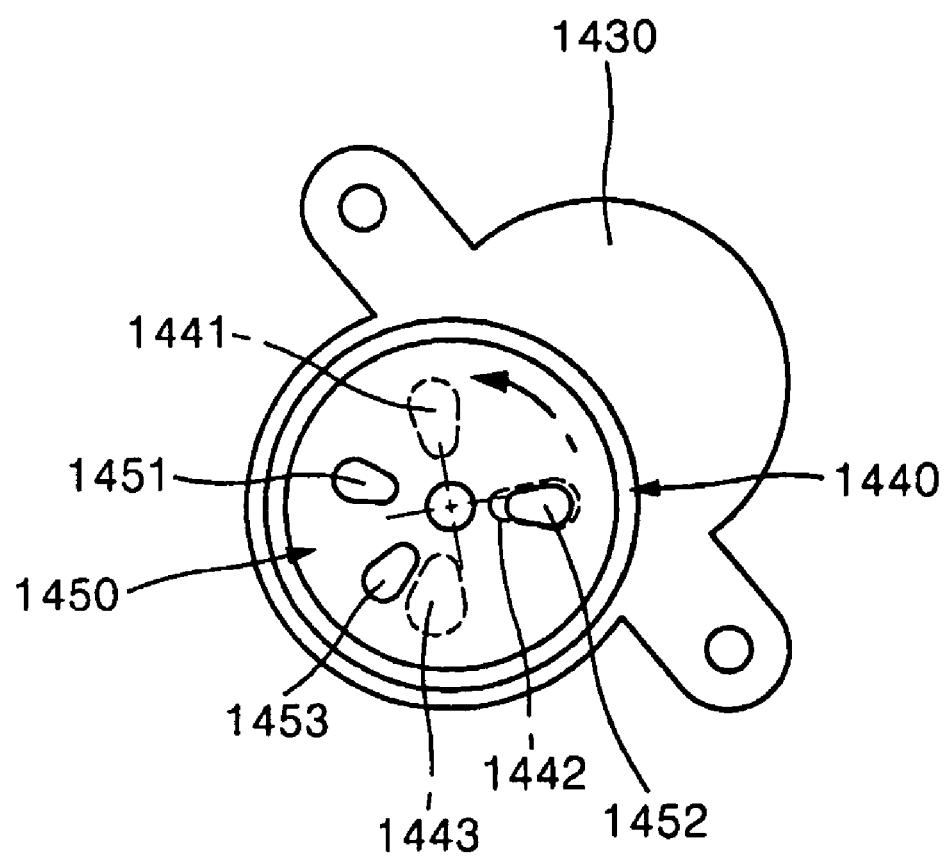
FIG. 7b is a cross-sectional view of the waterway converter.
Figure 7C:
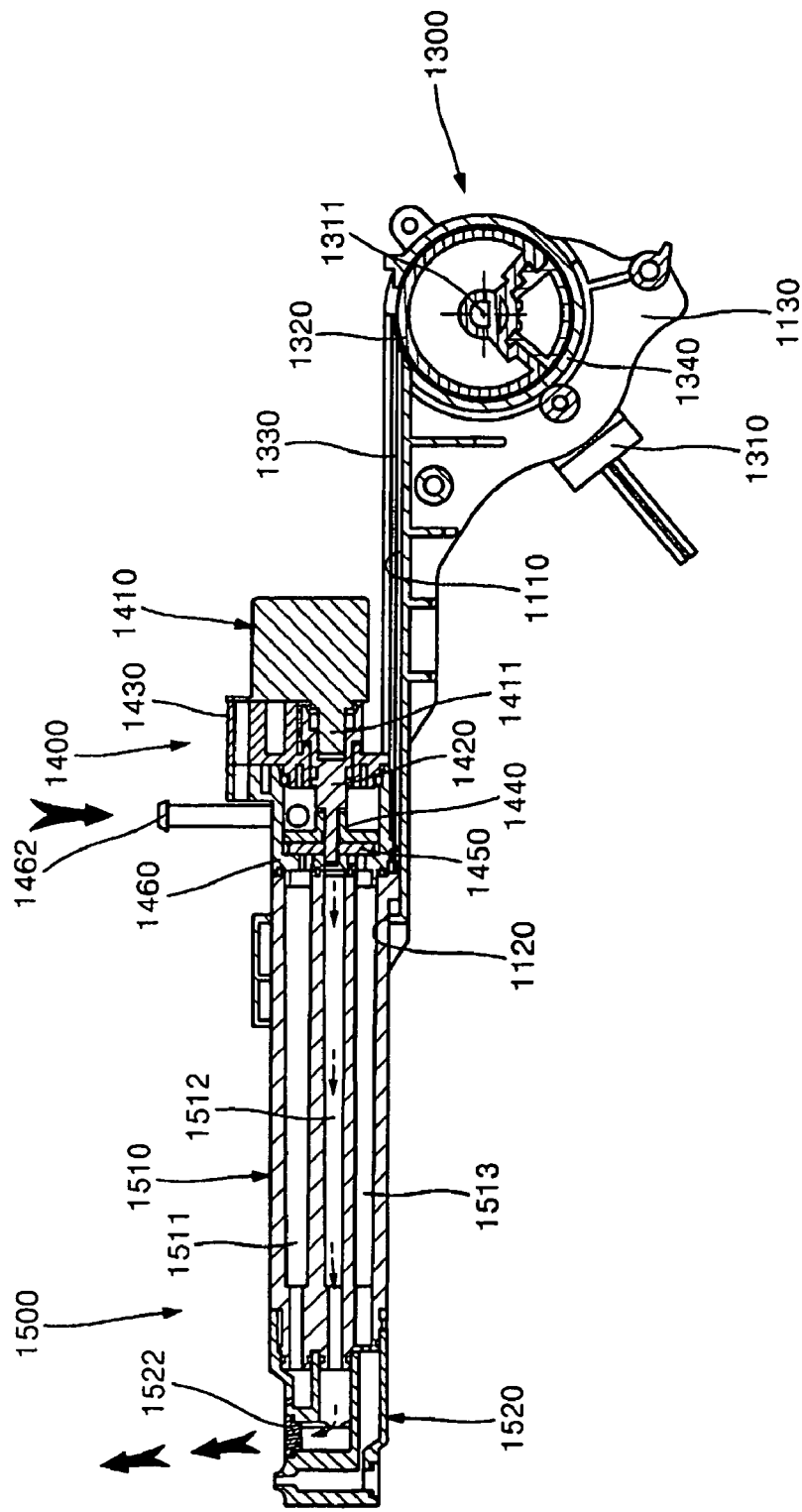
FIG. 7c is a cross-sectional view of the waterway converter where the cleansing water passed through the waterway converter is sprayed to the spray cap.
Figure 8A:
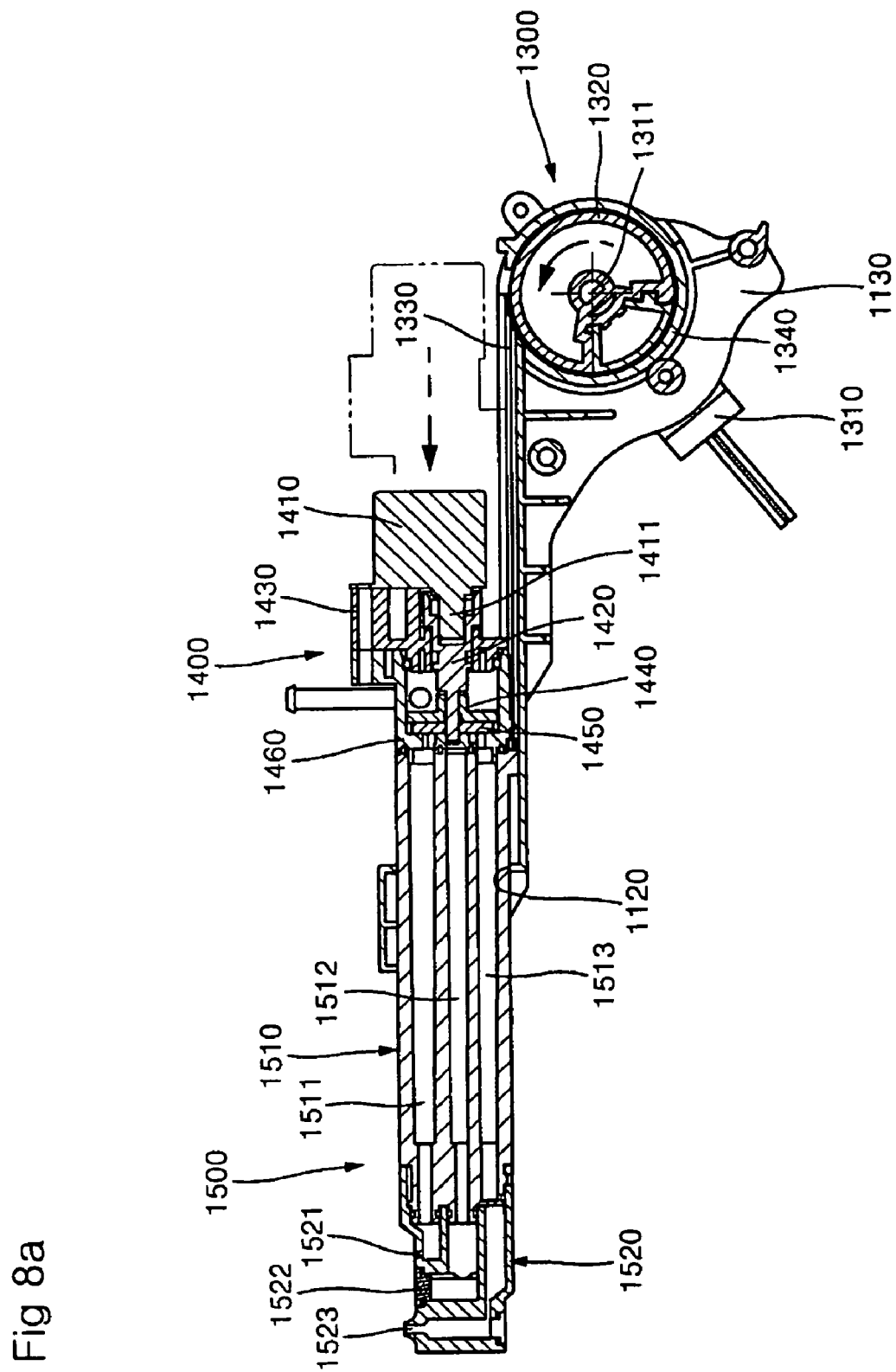
FIG. 8a shows the movement of the nozzle in the support for carrying out the enema function.
Figure 8B:
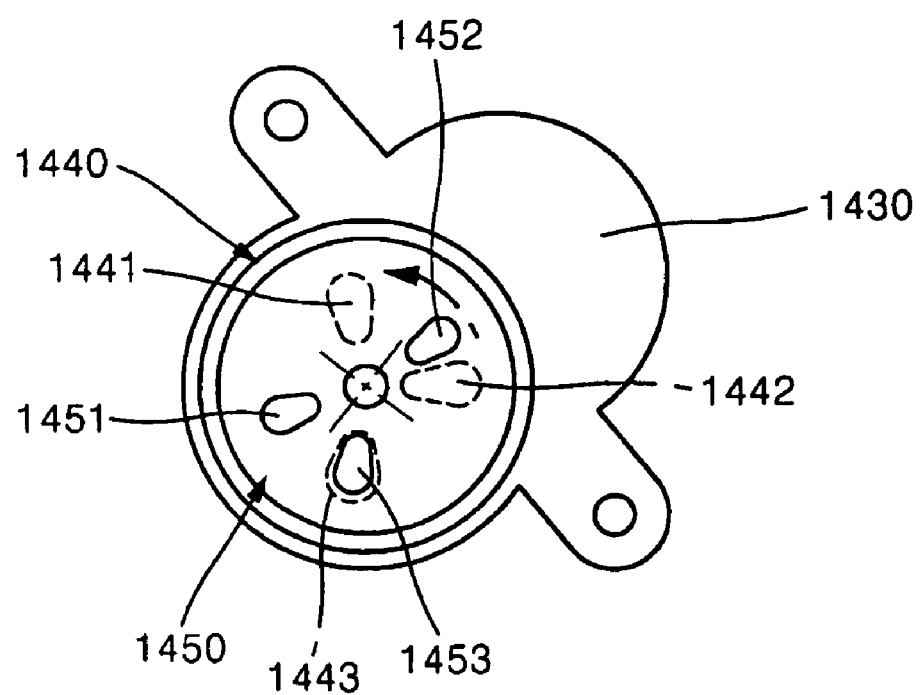
FIG. 8b is a cross-sectional view of the waterway converter.
Figure 8C:
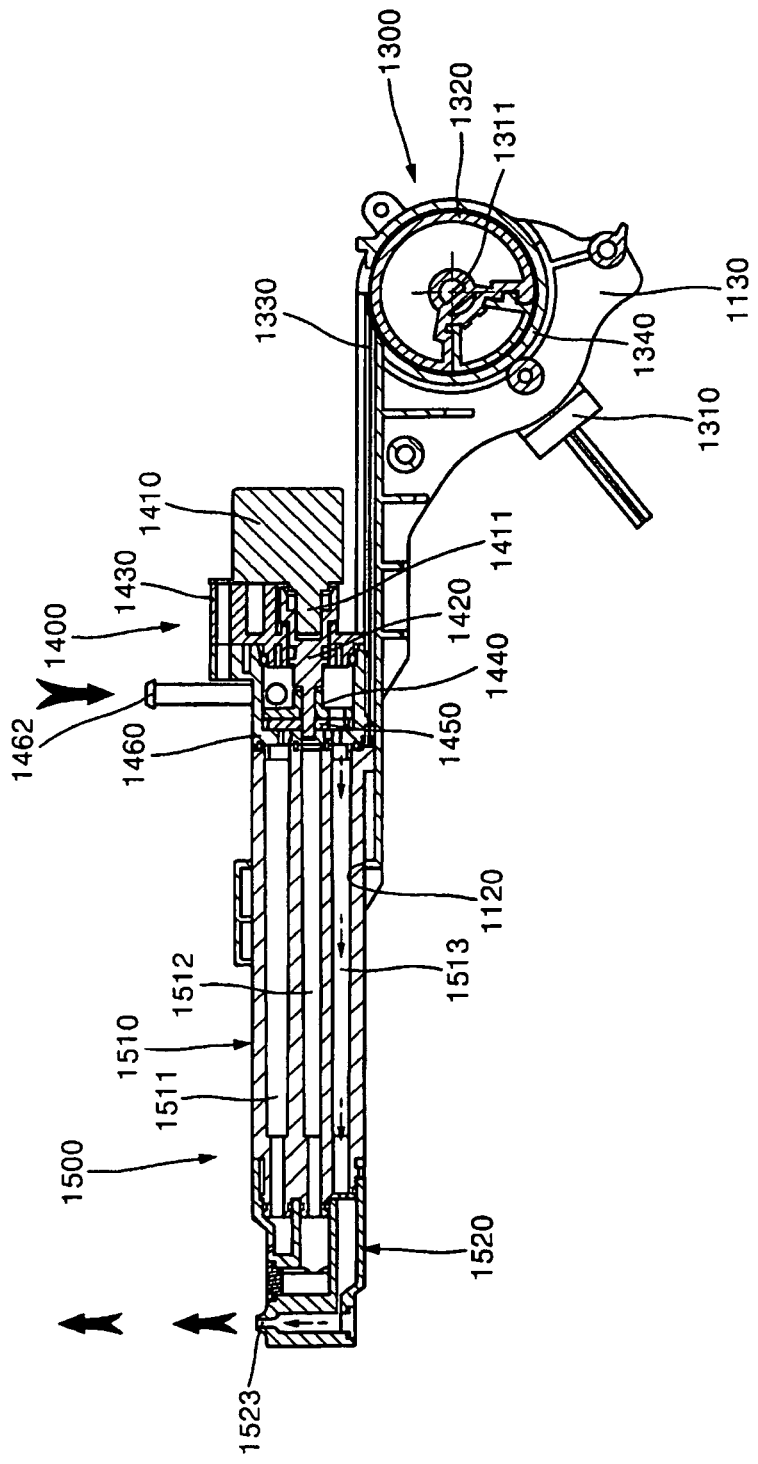
FIG. 8c is a cross-sectional view of the waterway converter where the cleansing water passed through the waterway converter is sprayed to the spray cap.
Figure 9:
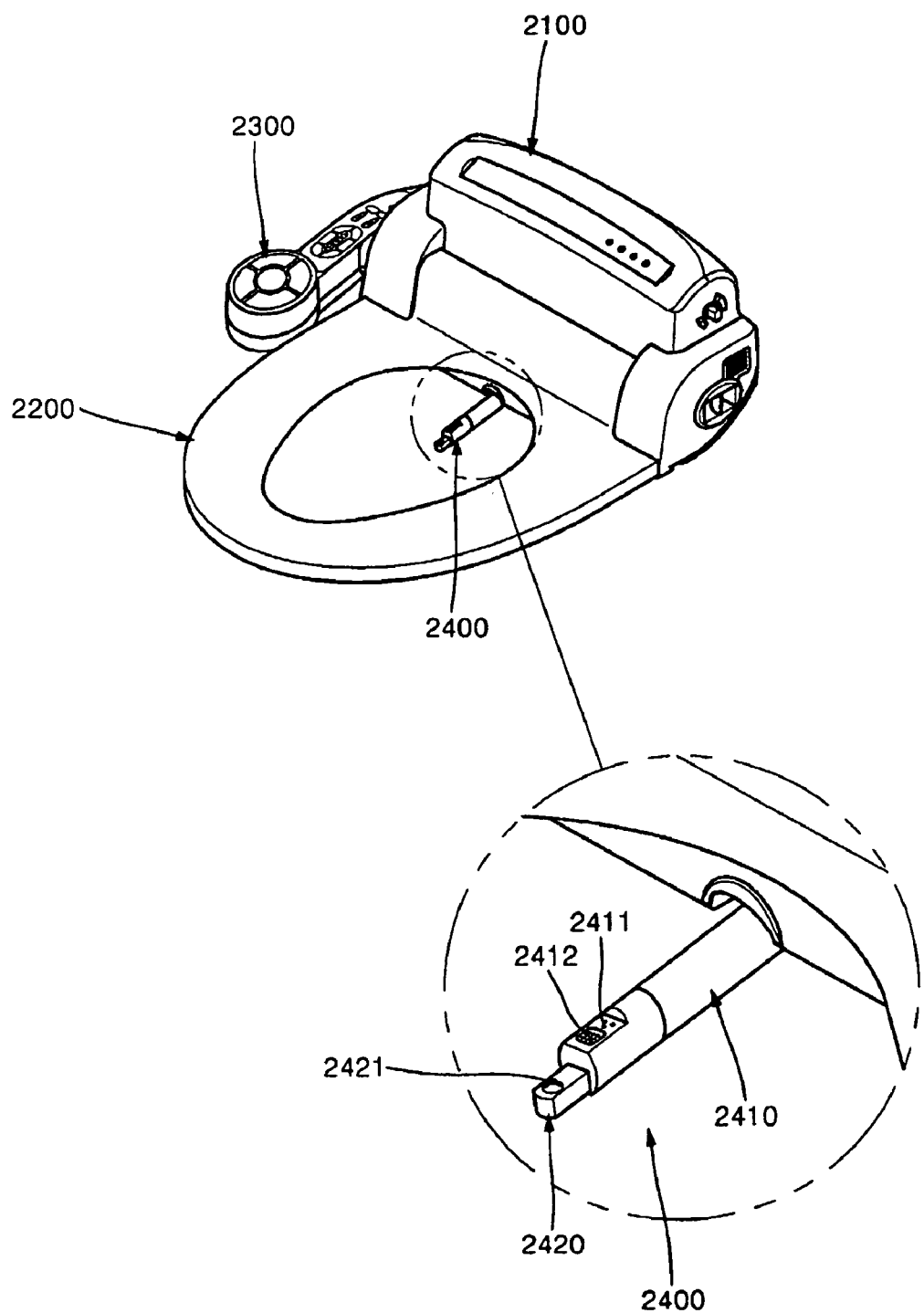
FIG. 9 is a partial enlarged view of the spraying nozzle structure according to a second embodiment of the invention.
Figure 10:
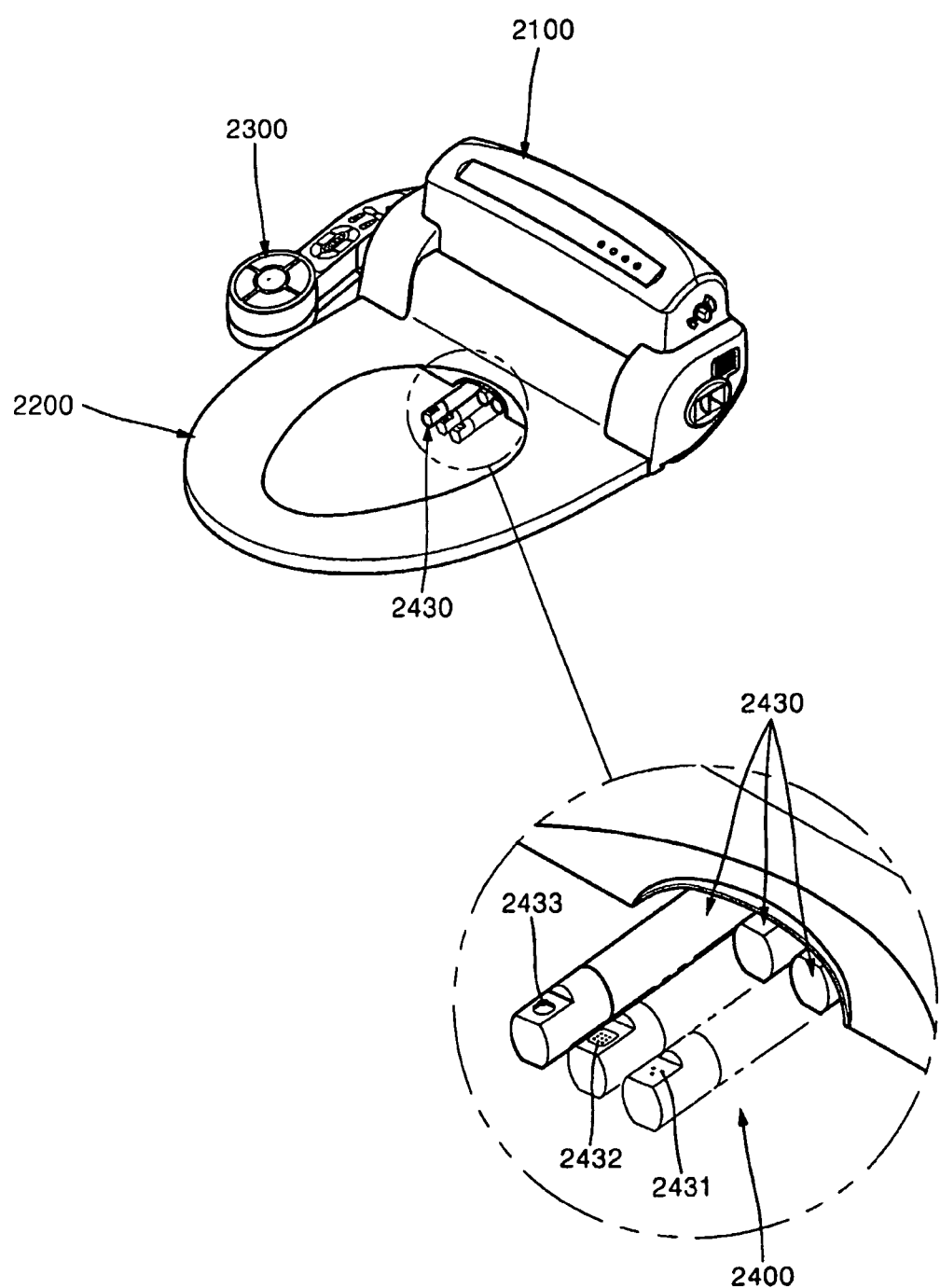
FIG. 10 is a partial enlarged view of the spraying nozzle structure in case of comprising three nozzles according to a third embodiment of the invention.
Figure 11:
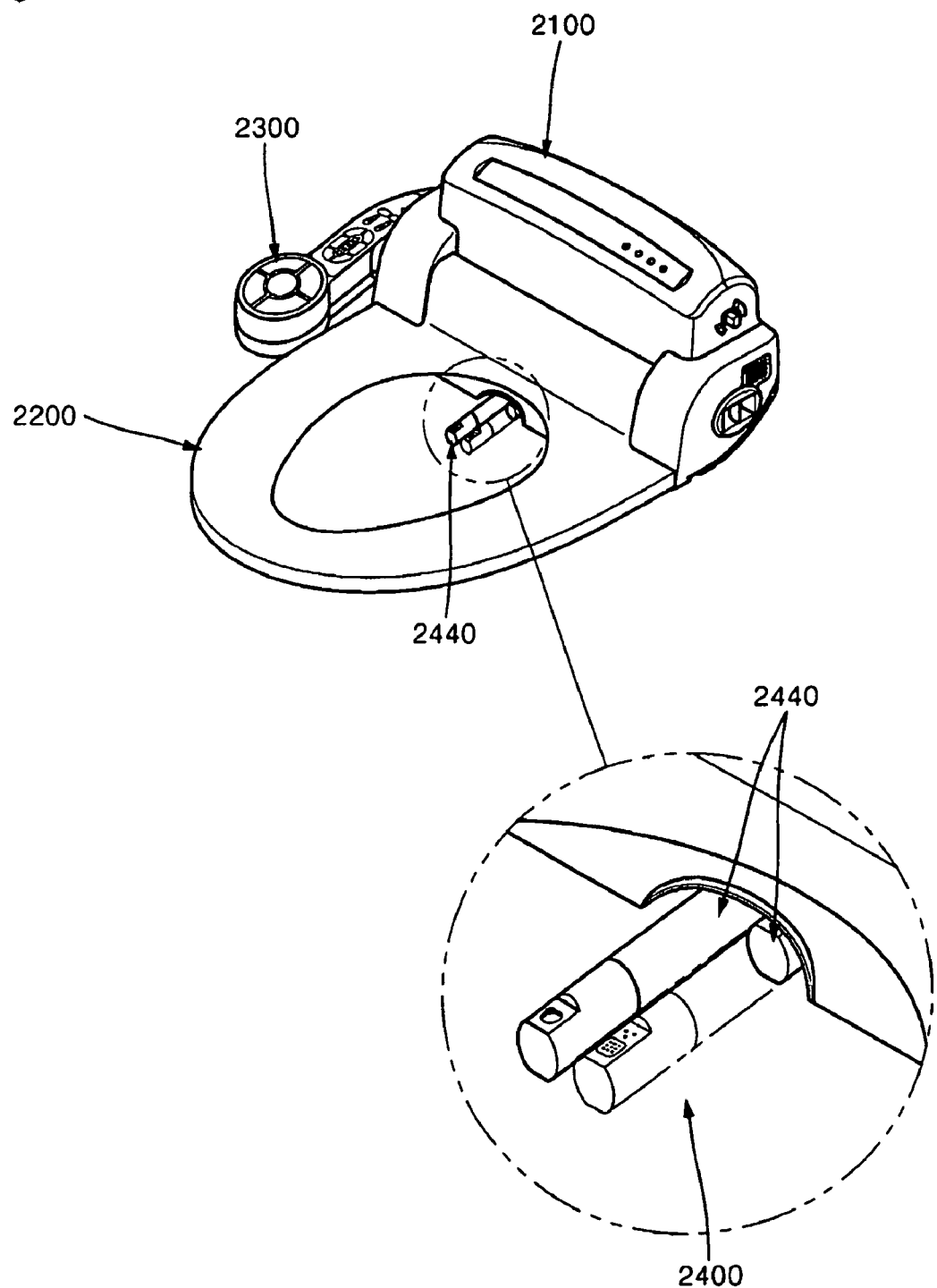
FIG. 11 is a partial enlarged view of the spraying nozzle structure in case of comprising two nozzles according to the third embodiment of the invention.
Figure 12:
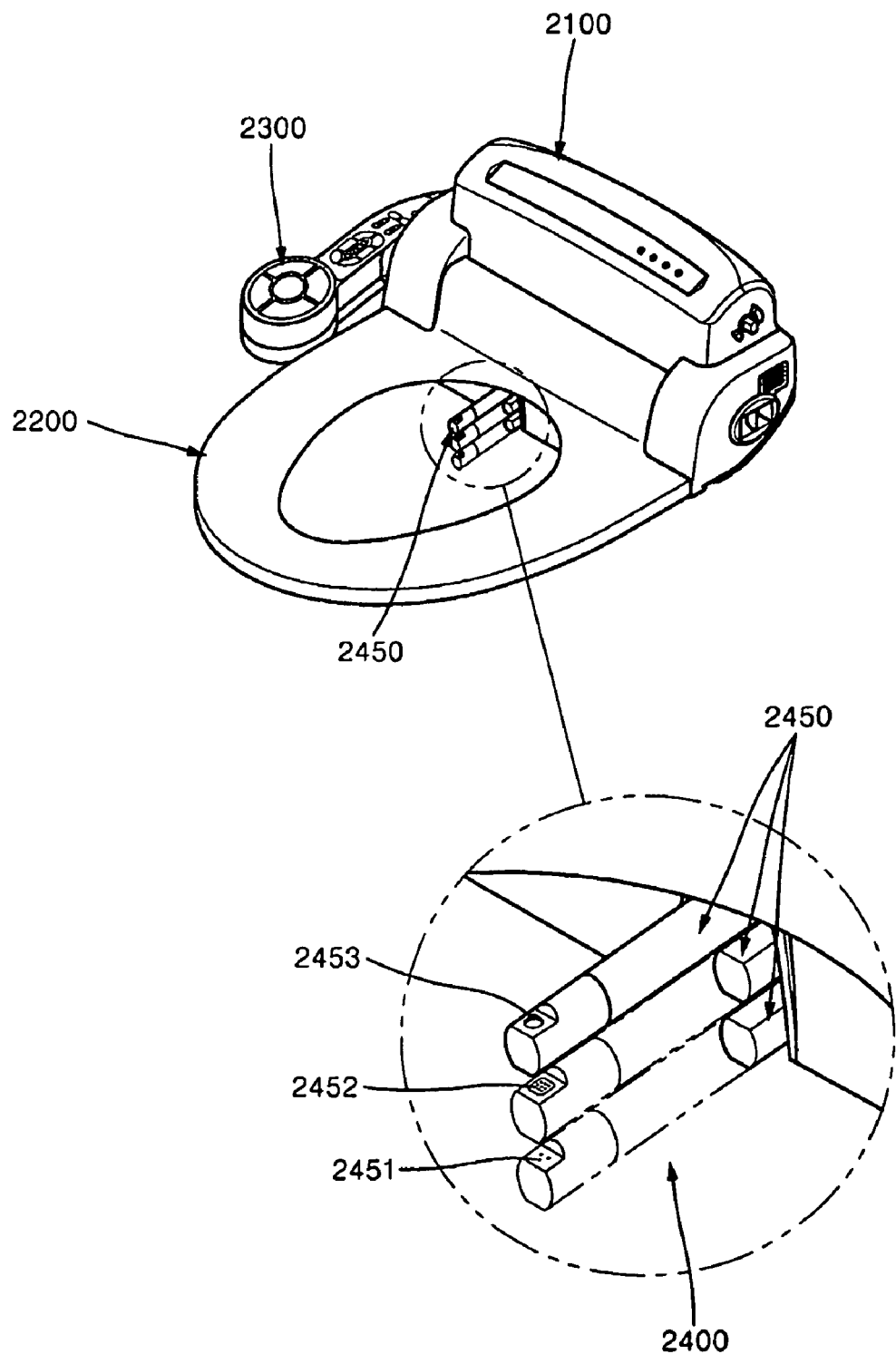
FIG. 12 is a partial enlarged view of the spraying nozzle structure in case of comprising three nozzles according to a fourth embodiment of the invention.
Figure 13:
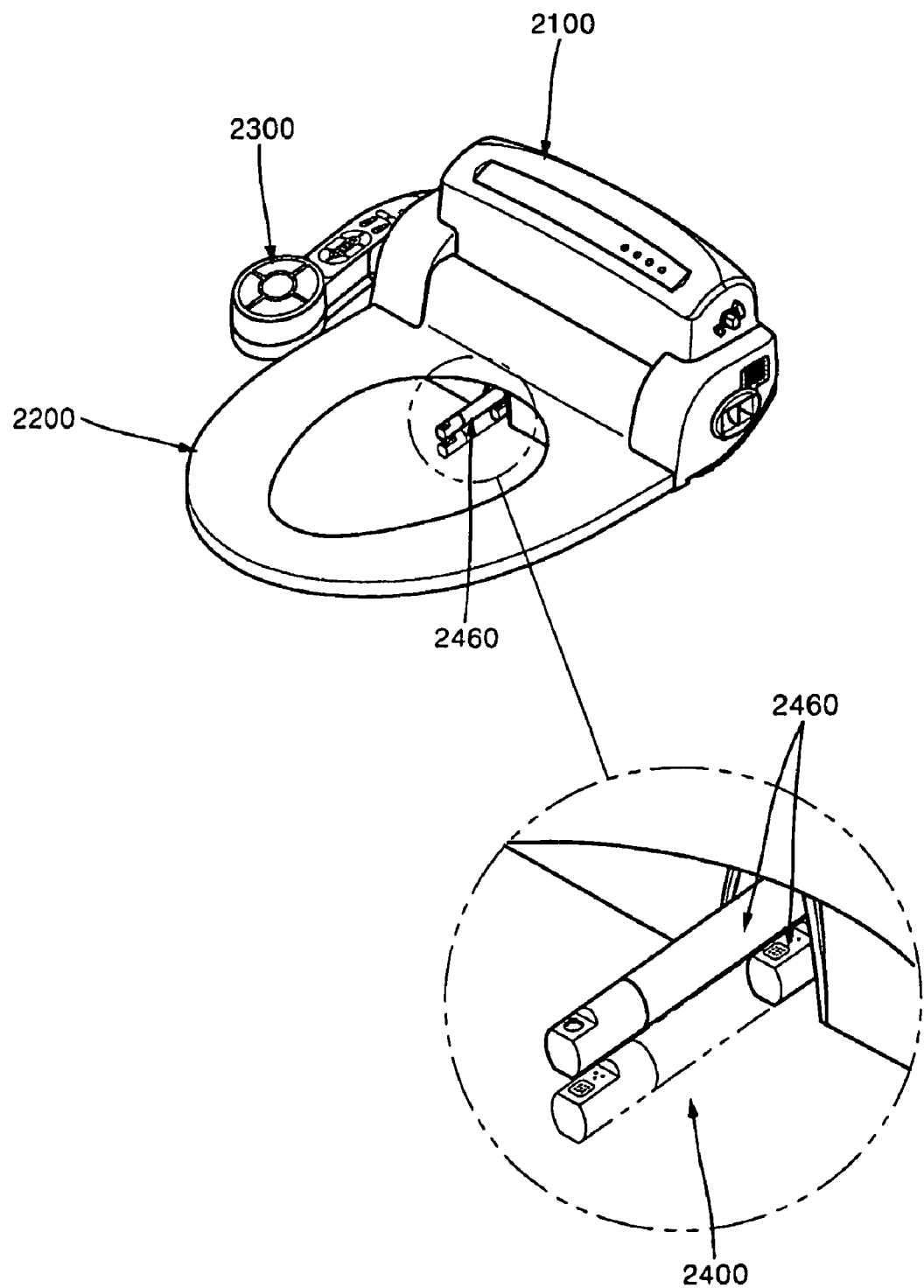
FIG. 13 is a partial enlarged view of the spraying nozzle structure in case of comprising two nozzles according to the fourth embodiment of the invention.
Figure 14:
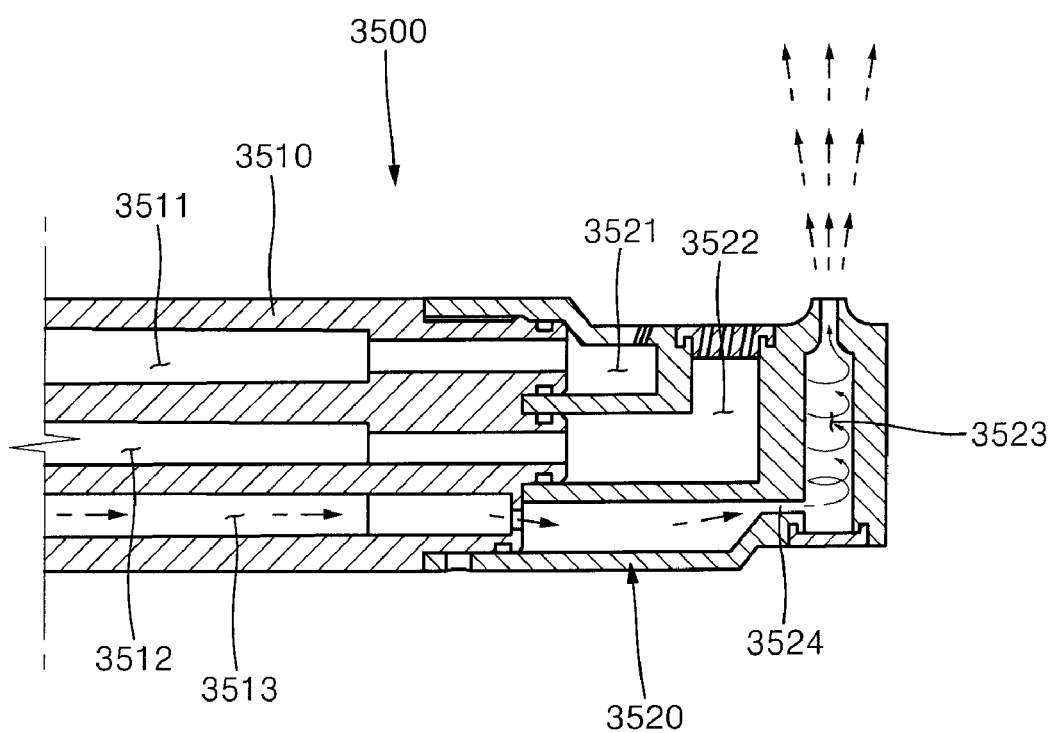
FIG. 14 is a cross-sectional view of a common spraying nozzle.
Figure 15:
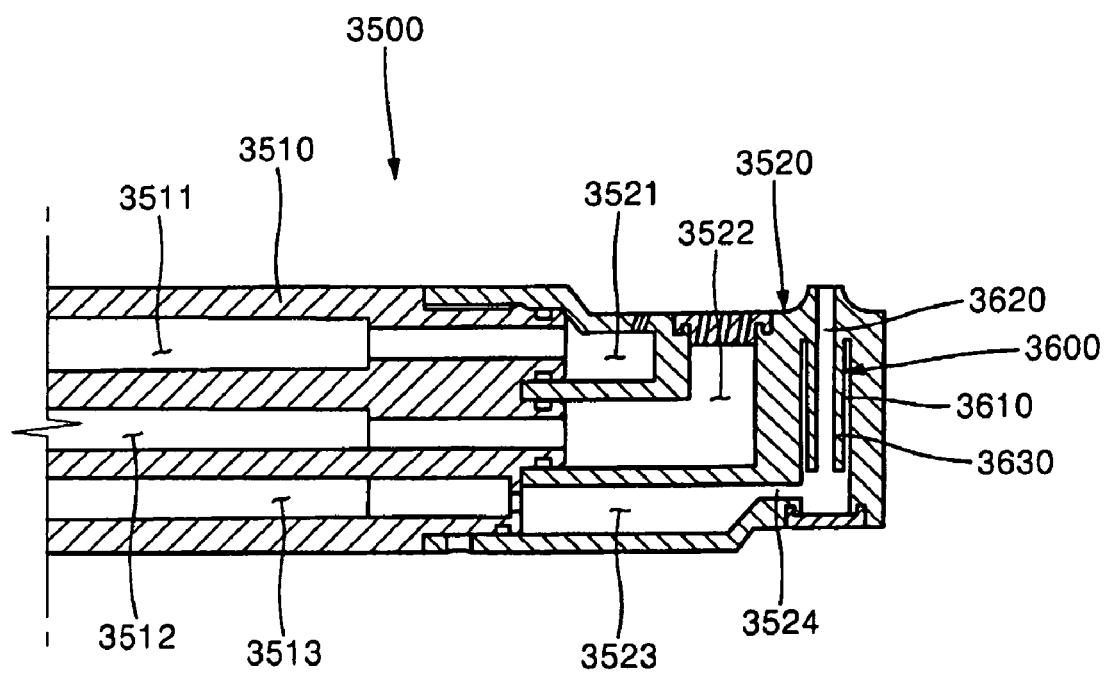
FIG. 15 is a cross-sectional view of a spray nozzle for the enema hole according to the embodiment of the invention.

FIG. 2a and FIG. 2b are an exploded perspective view of a first embodiment of the invention, and FIG. 3 is a cross-sectional side view of the first embodiment of the invention when assembled. FIG. 4 is a cross-sectional front view of the first embodiment of the invention when assembled, and FIG. 5 is a perspective view of the first embodiment of the invention when installed. FIG. 6 shows the operational state of an anal cleaning mode of the first embodiment. That is, FIG. 6a shows the movement of the nozzle in the support so as to cleanse anal region, FIG. 6b is a cross-sectional view of the waterway converter, and FIG. 6c is a cross-sectional view of the waterway converter where the cleansing water passed through the waterway converter is sprayed to the spray cap. FIG. 7 shows an operation of a bidet cleansing mode of the first embodiment. That is, FIG. 7a shows the movement of the nozzle in the support for carrying out the bidet cleansing, FIG. 7b is a cross-sectional view of the waterway converter, and FIG. 7c is a cross-sectional view of the waterway converter where the cleansing water passed through the waterway converter is sprayed to the spray cap. FIG. 8 shows an operation of an enema mode of the first embodiment. That is, FIG. 8a shows the movement of the nozzle in the support for carrying out the enema function, FIG. 8b is a cross-sectional view of the waterway converter, and FIG. 8c is a cross-sectional view of the waterway converter where the cleansing water passed through the waterway converter is sprayed to the spray cap. FIG. 9 is a partial enlarged view of the spraying nozzle structure according to a second embodiment of the invention. FIG. 10 is a partial enlarged view of the spraying nozzle structure in case of comprising three nozzles according to a third embodiment of the invention. FIG. 11 is a partial enlarged view of the spraying nozzle structure in case of comprising two nozzles according to the third embodiment of the invention. FIG. 12 is a partial enlarged view of the spraying nozzle structure in case of comprising three nozzles according to a fourth embodiment of the invention, and FIG. 13 is a partial enlarged view of the spraying nozzle structure in case of comprising two nozzles according to the fourth embodiment of the invention. FIG. 14 is a cross-sectional view of a common spraying nozzle, and FIG. 15 is a cross-sectional view of a spray nozzle for the enema hole according to the embodiment of the invention.

As shown in FIGS. 2a to 8c, the bidet according to the first embodiment of the invention comprises a support 1100 mounted on the bottom face of a bidet body 1070, a selection button 1210 mounted in one side of the bide body and for selecting an anal cleansing, a bidet cleansing, an enema function, a controller 1200 with a stop button 1220 for interrupting the function selected by the selection button 1210, an operator 1300 connected to the end portion of the support 1100 and for moving a three-directional nozzle 1500 correspondingly so as to carry out the function selected by the controller 1200, a waterway converter 1400 for converting the waterway in order to provide cleansing water according to the function selected in the controller 1200, and a three-directional nozzle 1500, which moves to a sliding space 1110 in the support 1100 to perform the function selected in controller 1200, and sprays the cleansing water passed through the waterway converter 1400. The construction of the above bidet having an enema function will be hereafter explained in greater detail.

The support 1100 is provided with the sliding space 1110 where the three-directional nozzle 1500 slides thereon. The sliding space 1110 is mounted slantedly on the bottom face of the bidet body 1070. The support 1100 is provided with a guidance space 1120 provided at the other end portion of the sliding space 1110 and for preventing escape of the three-directional nozzle sliding on the sliding space 1110. The support 1100 is provided with a support plate 1130 integrally provided and having a support hole 1140 fluid-communicatively formed vertically to an end portion of the sliding space 1110.

The operator 1300 is provided with an operating motor 1310 affixed to one side of the support plate 1130 such that a rotating axle 1311 is projected in the support hole 1140 of the support 1100. The operating motor 1310 is clockwise or counterclockwise rotated in order for the three-directional nozzle 1500 to be located correspondingly to the function selected in the controller 1200. The operator 1300 is provided with a take-up member 1320 combined with the rotating axle 1311 of the operating motor 1310 and being rotated in the same manner of the operating motor 1310. Here, an accommodating member 1340 affixed to the other side of the support plate 1130 receives the take-up member 1320 so as to prevent a leaf spring 1330 wound around the take-up member 1320 from escaping.

The waterway converter 1400 is provided with a stepping motor 1410 having a rotating axle 1411 projected therefrom. The rotating axle 1411 is clockwise or counterclockwise rotated so as to supply a cleaning water to the function selected in the controller 1200. The waterway converter 1400 is provided with a connection member 1420 connected to the rotating axle 1411 of the stepping motor 1410 and being rotated in the same manner as the stepping motor 1410. The waterway converter 1400 is provided with a fixed member 1430 mounted on one side of the stepping motor 1410 and receiving the connection member 1420 such that the end portion of the connection member 1420 is projected. The waterway converter is provided with a guidance member 1440 connected to a projected portion from the fixed member 1420 in order for the connection member 1420 to be freely rotated. The guidance member 1440 has a cleansing guide hole 1441, a bidet guide hole 1442, and an enema guide hole 1443 fluid-communicatively formed in the inner side thereof, and a conversion member 1450 connected to an end portion of the connection member 1420 and closely contacted with the guidance member 1440. The waterway converter is provided with the conversion member 1450 having a cleansing drain hole 1451, a bidet drain hole 1452, and an enema drain hole 1453 fluid-communicatively formed such that the direction of the cleaning water is fluid-communicated respectively with the cleansing guide hole 1441, the bidet guide hole 1442, and the enema guide hole 1443 of the guidance member 1440 according to the rotation of the stepping motor 1410. The waterway converter is provided with a support member 1460 for receiving the guidance member 1440 mounted on the connection member 1420 and the conversion member 1450 in the inside of a body 1461 such that the outer circumferential face of the guidance member 1440 is tightly contacted with the inner circumferential face of the body 1461. The body 1461 has an inlet hole 1462 projected on the outer circumferential face thereof for in-flowing the cleaning water. Here, a moving hole 1463 is fluid-communicatively formed in a side face of the body 1461 so as to be fluid-communicated respectively with the cleansing drain hole 1451, the bidet drain hole 1452, and the enema drain hole 1453. The waterway converter is provided with a packing 1470 mounted on the outer circumferential face of the moving hole 1463 of the support member 1460.

The guidance member 1440 is constructed in such a manner that the bidet guide hole 1442 is fluid-communicatively formed at the position perpendicularly crossing the center of the cleansing guide hole 1441 fluid-communicatively formed in the upper portion of the guidance member 1440, and the enema guide hole 1443 is fluid-communicatively formed at the position facing the cleansing guide hole 1441.

The conversion member 1450 is constructed in such a manner that the cleansing drain hole 1451 and the enema drain hole 1453 are fluid-communicatively formed between the cleansing guide hole 1441 and the enema guide hole 1443, and the bidet drain hole 1452 is fluid-communicatively formed between the bidet guide hole 1442 and the enema guide hole 1443.

The three-directional nozzle 1500 is provided with a cleansing water moving pipe 1510 connected to an end portion of the support member 1460 so as to receiving the packing 1470 of the waterway converter 1400. The three-directional nozzle 1500 is provided with the cleansing water moving pipe having a cleansing moving hole 1511, a bidet moving hole 1512, and an enema moving hole 1513 fluid-communicatively formed so as to lie in the same line as the cleansing guide hole 1441, the bidet guide hole 1442, and the enema guide hole 1443. The three-directional nozzle 1500 is provided with a spraying cap 1520 connected to an end portion of the cleansing water moving pipe 1510 and having a cleansing spraying hole 1521, a bidet spraying hole 1522, and an enema spraying hole 1523 fluid-communicatively formed so as to be fluid-communicated with the cleansing moving hole 1511, the bidet moving hole 1512, and the enema moving hole 1513.

The assembling process of the first embodiment of the inversion will be hereafter explained below.

First, the operating motor 1310 of the operator 1300 is tightly contacted to one side of the support plate 1130 of the support 1300, then the rotating axle 1311 of the operating motor 1310 is fixed to one side of the support plate 1130 in order to penetrate to the support hole 1140 of support plate 1130. Then, a leaf spring 1330 is connected to the rotating axle 1311 of the protracted operating motor 1310, and a take-up member 1320 is installed in the sliding space 1110 of the support 1100. The take-up member 1320 is housed in a housing member 1340 and is fixed to the other side face of the support plate 1130.

In addition, a connection member 1420 is mounted on the rotating axle 1411 of the stepping motor 1410 of the waterway converter 1400. By housing the connection member 1420, a fixed member 1430 is closely contacted to the stepping motor 1410 in order for the end portion thereof to be protracted. A guide member 1440 and a conversion member 1450 are installed at the protracted connection member 1420 through the fixed member 1430.

At this time, as shown in FIG. 4, in the state that the cleansing guide hole 1441, the bidet guide hole 1442, and the enema guide hole 1443 of the guidance member 1440 are not fluid-communicatively connected with the cleansing drain hole 1451, the bidet drain hole 1452, and the enema drain hole 1453 of the conversion member 1450, a fixed member 1430 is tight-contactedly connected with the body of the support member 1460 such that the outer circumferential face of the guidance member 1440 is closely contacted to the inside of the body of the support member 1460. A packing 1470 is mounted on the inner side of the support member 1460.

On the other hand, a cleansing water moving pipe 1510 is closely contacted to the cross-section of the support member 1460 in which the packing 1470 is installed. Then, the cleansing water moving pipe 1510, the support member 1460, and the stepping motor 1410 are fixed using screws.

The three-directional nozzle 1500, in which the spray cap 1520 is mounted on the end portion of the cleansing water moving pipe 1510, is projected into the guidance space 1120 through the sliding space 1110 of the support 1100. In this state, the leaf spring 1330 is connected to the lower end portion of the cleansing water moving pipe 1510.

As mentioned above, the support 1100 with the three-directional nozzle 1500 assembled therewith is installed in the inner side of the bidet body 1070. The controller 1200 is assembled to one side of the bidet body 1070. The operator 1300 and the waterway converter 1400 are connected to the controller in order to transmit the signals. The assembly is rested on the bidet body, as shown in FIG. 5.

Hereafter, the procedures of using the first embodiment of the invention, which is assembled as described above, is explained.

First, the power is turned on so as to be able to transmit the signals from the controller 1200, the operator 1300, and the waterway converter 1400. In case where a user finishes his or her relief and needs an anus cleansing, an anal cleansing button 1211 of the controller 1200 is pushed. The signal from the pressed anus-cleansing button 1211 is transmitted to the operator 1300 by means of the control of the controller 1200. As shown in FIG. 6a, the operating motor 1310 of the operator 1300 rotates in clockwise direction. The take-up member 1320, which is connected to the rotating axle 1311 of the operator motor 1310, rotates; at the same time, the leaf spring 1330, which is wound around the take-up member 1320, is pushed and moved to the sliding space 1110 of the support 1100.

At this time, the three-directional nozzle, which is connected to the end portion of the leaf spring 1330, rotates as much as the predefined angle of the operating motor 1310. The three-directional nozzle 1500 is projected to the guide space 1120 of the support 1100 and placed in a position to cleanse anus.

In this way, when the three-directional nozzle 1500 is positioned in the position to cleanse anus, the operating motor 1310 stops its rotation by the control of the controller 1200. Based on the arrangement of FIG. 4, the stepping motor 1410 of the waterway converter 1400 is rotated clockwise at a predefined angle such that the connection member 1420, which is connected to the rotating axle 1411 of the stepping motor 1410 is rotated, as shown in FIG. 6b. At the same time, the conversion member 1450 connected to the connection member 1420 is rotated such that a cleansing drain hole 1451 of the conversion member 1450, a cleansing guide hole 1441 of the guide member 1440, and a cleansing moving hole 1551 of the cleansing water moving pipe 1510 are fluid-communicated. Then, by the control of the controller 1200, the cleansing water stored in the water container of the bidet body 1070 is supplied.

The cleansing water supplied as described above is inflown inside the body 1461 through the inlet 1462 of the support member 1460. Then, via the communicated cleansing guide hole 1441 of the guide member and the communicated cleansing drain hole 1451 of the conversion member 1450, as shown in FIG. 6c, the cleansing water is ejected to a cleansing spraying hole 1521 of the spraying cap 1520 through a cleansing moving hole 1511 of the cleansing moving pipe 1510, thereby cleansing the anal region.

On the other hand, when the predefined time is expired or the anus cleansing function is completed, a user can push a stop button 1220 of a controller 1200 in order to stop the spraying of the cleansing water.

At this time, the stepping motor, which is rotated in a positive direction by the control of the controller 1200, is rotated in a reverse direction. Then, the conversion member 1450, which is connected to the stepping motor 1410, is rotated in a reverse direction such that the cleansing guide hole 1441 of the guide member 1440, the cleansing drain hole 1451 of the conversion member 1450, and the cleansing moving hole of the cleansing water moving pipe 1510 is closed. Simultaneously, the operating motor 1310 of the operator 1300 is rotated in a reverse direction, and the take-up member 1320, which is connected to the rotating axle 1311 of the operating member 1310, is rotated in a reverse direction, so that the leaf spring 1330, which is moved into the sliding space 1110, is wound in order for the three-directional nozzle 1500 to be restored to its original state, thereby standing by for the next operation.

In addition, when the user relieves himself or herself and needs a bidet cleansing, a bidet-cleansing button 1212 of the controller 1200 is pressed. Then, the signal of the pressed bidet-cleansing button 1212 is delivered to the operator 1300 by the control of the controller 1200. As shown in FIG. 7a, the operating motor 1310 of the operator 1300 is rotated in a positive direction, and the take-up member 1320 connected to the rotating axle 1311 of the rotating operating motor 1310 is rotated. At the same time, the leaf spring 1330, which is wound around the take-up member 1320, is pushed toward the sliding space 1110 of the support 1100.

At this time, the three-directional nozzle 1550, which is connected to the end portion of the leaf spring 1330, is rotated as much as the predetermined angle of the operating motor 1310. Therefore, the three-directional nozzle 1550 is projected to a guide space 1120 of the support 1100 to be positioned so as to carrying out a bidet cleansing.

In this way, when the three-directional nozzle 1500 is positioned for a bidet cleansing, the rotation of the operating motor 1310 is stopped by the control of the controller 1200. In the configuration of the FIG. 4, the stepping motor 1410 of the waterway converter 1400 is rotated in a reverse direction to the predefined angle. Then, as shown in FIG. 7b, the conversion member 1450, which is connected to the connection member 1420, is rotated such that the bidet drain hold 1452 of the conversion member 1450, a bidet guide hole 1442 of the guide member 1440, and a bidet moving hole 1512 of the cleansing water moving pipe 1510 are all fluid-communicated. Then, by the control of the controller 1200, the cleansing water stored in the water container of the bidet body 1070 is supplied.

The cleansing water supplied as described above is inflown inside the body 1461 through the inlet 1462 of the support member 1460. Then, via the communicated bidet guide hole 1442 of the guide member 1440 and the bidet drain hole 1452 of the conversion member 1450, as shown in FIG. 7c, the cleansing water is smoothly ejected to a cleansing spraying hole 1521 of the spraying cap 1520 through a bidet moving hole 1512 of the cleansing moving pipe 1510, thereby cleansing the anal region.

On the other hand, when the predefined time is expired or the bidet cleansing function is completed, a user can push a stop button 1220 of a controller 1200 in order to stop the spraying of the cleansing water.

At this time, the stepping motor 1410, which is rotated in a positive direction by the control of the controller 1200, is rotated in a reverse direction. Then, the conversion member 1450, which is connected to the stepping motor 1410, is rotated in a reverse direction such that the bidet guide hole 1442 of the guide member 1440, the bidet drain hole 1452 of the conversion member 1450, and the bidet moving hole 1512 of the cleansing water moving pipe 1510 is closed to shut off the supply of the cleansing water. Simultaneously, the operating motor 1310 of the operator 1300 is rotated in a reverse direction, and the take-up member 1320, which is connected to the rotating axle 1311 of the operating member 1310, is rotated in a reverse direction, so that the leaf spring 1330, which is moved into the sliding space 1110, is wound in order for the three-directional nozzle 1500 to be restored to its original state, thereby standing by for the next operation.

Furthermore, if a constipated user pushes an enema button 1213 of the controller 1200 in order to relieve himself or herself, then, the signal of the enema button 1213 is transmitted to the operator 1300 by the control of the controller 1200. As shown in FIG. 8a, the operating motor 1310 of the operator 1300 is rotated in a positive direction, and the take-up member 1320 connected to the rotating axle 1311 of the rotating operating motor 1310 is rotated. At the same time, the leaf spring 1330, which is wound around the take-up member 1320, is pushed toward the sliding space 1110 of the support 1100.

At this time, the three-directional nozzle 1550, which is connected to the end portion of the leaf spring 1330, is rotated as much as the pre-set angle of the operating motor 1310. Therefore, the three-directional nozzle 1550 is projected to a guide space 1120 of the support 1100 to be positioned so as to carrying out an enema function.

In this way, when the three-directional nozzle 1500 is positioned for an enema function, the rotation of the operating motor 1310 is stopped by the control of the controller 1200. In the configuration of the FIG. 4, the stepping motor 1410 of the waterway converter 1400 is rotated in a reverse direction to the predefined angle. Then, as shown in FIG. 8b, the conversion member 1450, which is connected to the connection member 1420, is rotated such that the enema drain hold 1453 of the conversion member 1450, an enema guide hole 1443 of the guide member 1440, and an enema moving hole 1513 of the cleansing water moving pipe 1510 are all fluid-communicated. Then, by the control of the controller 1200, the cleansing water stored in the water container of the bidet body 1070 is supplied.

The cleansing water supplied as described above is inflown inside the body 1461 through the inlet 1462 of the support member 1460. Then, via the communicated enema guide hole 1443 of the guide member 1440 and the enema drain hole 1453 of the conversion member 1450, as shown in FIG. 8c, the cleansing water is discharged with a high pressure to an enema spraying hole 1521 of the spraying cap 1520 through an enema moving hole 1512 of the cleansing moving pipe 1510. Therefore, the high-pressure cleansing water stimulates the user's anus and is introduced into the inside of the rectum, thereby performing the enema function.

On the other hand, when the user pushed the stop button 1220 of a controller 1200 in order to stop the enema function, the stepping motor 1410, which is rotated in a reverse direction by the control of the controller 1200, is rotated in a positive direction. Then, the conversion member 1450, which is connected to the stepping motor 1410, is rotated in a reverse direction such that the enema guide hole 1443 of the guide member 1440, the enema drain hole 1453 of the conversion member 1450, and the enema moving hole 1513 of the cleansing water moving pipe 1510 is closed to shut off the supply of the cleansing water. Simultaneously, the operating motor 1310 of the operator 1300 is rotated in a reverse direction, and the take-up member 1320, which is connected to the rotating axle 1311 of the operating member 1310, is rotated in a reverse direction, so that the leaf spring 1330, which is moved to the inside of the sliding space 1110, is wound in order for the three-directional nozzle 1500 to be restored to its original state, thereby standing by for the next operation.

Next, according to a second embodiment of the invention, a nozzle tip having one function among the three functions of cleansing, bidet, and enema is accommodated inside the main body of the spray nozzle having the rest functions only such that it can be separately projected.

Specifically, in the second embodiment of the invention, among a cleansing hole for spraying a cleansing water, a bidet hole for spraying a cleansing water for bidet-cleaning, and an enema hole for spraying enema liquid (water), two selected spray holes is fluid-communicatively formed in the upper end face of a spray nozzle body. At one side of the leading edge of the spray nozzle body, the unselected one spray hole among the cleansing, bidet, and enema holes is fluid-communicatively formed in the upper end face thereof so that the spray tip is projectably inserted.

According to the second embodiment of the invention, in case where the enema function is constructed in a separately projectable way, as shown in FIG. 9, a cleansing hole 2411 and a bidet hole 2412 is fluid-communicatively formed in the spray nozzle body 2410. At one side of the leading end of the spray nozzle body 2410, an enema hole 2421 is fluid-communicatively formed in the upper end face thereof so that the spray tip 2420 is projectably inserted and housed.

In addition, in case where the bidet cleansing function is constructed in a separately projectable way, a cleansing hole and an enema hole is fluid-communicatively formed in the spray nozzle body. At one side of the leading end of the spray nozzle body, a bidet hole is fluid-communicatively formed in the upper end face thereof so that the spray tip is projectably inserted and housed. According to the second embodiment of the invention, in case where the anus cleansing function is constructed in a separately projectable way, a bidet hole and an enema hole is fluid-communicatively formed in the spray nozzle body. At one side of the leading end of the spray nozzle body, a cleansing hole 2411 is fluid-communicatively formed in the upper end face thereof so that the spray tip is projectably inserted and housed.

As understood from the above-described construction of the second embodiment, a cleansing hole and a bidet hole, or a bidet hole and an enema hole can be fluid-communicatively constructed on the top face of the spry nozzle body 2410. Accordingly, the spray tip 2420 can have respectively the enema hole, the bidet hole, and the cleansing hole formed fluid-communicatively therein.

Here, the cleansing hole/bidet holes, the cleansing hole/enema holes, and the bidet/enema holes provided in the spray nozzle body may be formed respectively of two spray holes, or constructed of a single spray nozzle such that it can spray the cleansing water with different pressures and in different directions to thereby carrying out two different functions.

With the bidet of the second embodiment having the above-described construction, in case where a user needs a function, which can be performed by one of the spray holes provided in the spray nozzle body, he or she presses a certain predetermined button on the controller 2300 so that the spray nozzle body is projected with a certain distance by the pressure of the water stored in the water container and the cleansing water of appropriate pressure is sprayed from a spray hole corresponding the selected function, thereby carrying out the cleansing function. When the user presses a certain button in the controller 2300 in order to operate a function, which can be performed by a spray hole provided in the spray tip, the spray nozzle body is projected with a certain distance by the pressure of the cleansing water stored in the water container and further the spray tip is projected from the leading edge of the spray nozzle body. Thereafter, the cleansing water having a certain appropriate pressure is sprayed from the spray hole on the spray tip to thereby carry out the corresponding cleansing work.

Next, according to a third embodiment of the invention, among the cleansing, bidet, and enema functions, selected one or two functions are embodied in two or three spray nozzles. The two or three spray nozzles are projectably inserted in the central lower portion of the bidet body such that they are arranged horizontally adjacent to one another.

Specifically, according to the third embodiment of the invention, two or three spay nozzles are projectably inserted in the lower portion of the center of the bidet body and arranged horizontally so as to be placed adjacent to one another. Each spray nozzle has one or two spray holes fluid-communicated therewith. The spay holes are selected from a cleansing hole for spraying a cleansing water for anus cleaning, a bidet hole for spraying a cleansing water for pubic-area cleaning, and an enema hole for spraying an enema water.

As understood from the above-described construction of the third embodiment of the invention and also is shown in FIG. 10, each of a cleansing hole 2431, a bidet hole 2432, and an enema hole 2433 may be constituted separately in each of three spray nozzles 2430. As shown in FIG. 11, two spray nozzles 2440 may be provided in such a manner that two spray holes selected from the cleansing, bidet, and enema holes are formed in one spray nozzle, and the remaining one spray hole is formed in the other spray nozzle.

As shown in FIG. 11, in case where total two spray nozzles 2440 are provided in such a way that two selected spray hole from the cleansing, bidet, and enema holes is fluid-communicatively formed in one spray nozzle 2440 and one remaining spray hole is fluid-communicatively formed in the other spray nozzle 2440, the spray nozzle having two spray holes, i.e., the cleansing/bidet holes, the cleansing/enema holes, and the bidet/enema holes may have two spray holes fluid-communicatively formed. Alternatively, a single spray hole is fluid-communicatively formed such that it can spray the cleansing water with different pressures and in different directions to thereby perform two different functions.

Next, according to a fourth embodiment of the invention, among the cleansing, bidet, and enema functions, selected one or two functions are embodied in two or three spray nozzles. The two or three spray nozzles are projectably inserted in the central lower portion of the bidet body such that they are arranged vertically adjacent to one another.

Specifically, according to the fourth embodiment of the invention, two or three spay nozzles are projectably inserted in the lower portion of the center of the bidet body and arranged vertically so as to be placed adjacent to one another. Each spray nozzle has one or two spray holes fluid-communicated therewith. The spay holes are selected from a cleansing hole for spraying a cleansing water for anus cleaning, a bidet hole for spraying a cleansing water for pubic-area cleaning, and an enema hole for spraying an enema water.

As understood from the above-described construction of the forth embodiment of the invention and also is shown in FIG. 12, each of a cleansing hole 2451, a bidet hole 2452, and an enema hole 2453 may be constituted separately in each of three spray nozzles 2450. As shown in FIG. 13, two spray nozzles 2460 may be provided in such a manner that two spray holes selected from the cleansing, bidet, and enema holes are formed in one spray nozzle, and the remaining one spray hole is formed in the other spray nozzle.

As shown in FIG. 13, in case where total two spray nozzles 2460 are provided in such a way that two selected spray hole from the cleansing, bidet, and enema holes is fluid-communicatively formed in one spray nozzle 2460 and one remaining spray hole is fluid-communicatively formed in the other spray nozzle 2460, the spray nozzle having two spray holes, i.e., the cleansing/bidet holes, the cleansing/enema holes, and the bidet/enema holes may have two spray holes fluid-communicatively formed. Alternatively, a single spray hole is fluid-communicatively formed such that it can spray the cleansing water with different pressures and in different directions to thereby perform two different functions.

With the bidet having the above-described construction according to the third and fourth embodiment of the invention, when a button of the controller 2300 corresponding to a desired function is pressed, a spray nozzle for the desired function is projected with a certain distance by means of the pressure of the cleansing water stored in the water container inside the body and then the cleansing water having an appropriate pressure is sprayed to carry out the cleansing function.

On the other hand, the conventional spray nozzle structure used in the conventional common bidet generates a turbulent current right before spraying, as shown in FIG. 14. Therefore, the conventional bidet cannot easily carry out an enema function, as in the embodiments of the invention having the above-described construction.

Therefore, a specially designed spray nozzle structure is needed in order to prevent the turbulent current and thus secure a higher-pressure of water, and avoid scattering of the sprayed water stream. The enema nozzle structure of the invention to meet these purposes will be explained below.

As shown in FIG. 15, a spray nozzle structure of the invention for a bidet having an enema function comprises a spray cap 3520 having an enema hole for carrying out an enema function. A guide groove 3610 is formed projectably downwardly from the upper portion of an enema spray hole 3523 so as to prevent turbulence of a cleansing water passing through the discharge hole 3524 formed inside the enema spray hole 3523 of the spray cap 3520. In addition, the spray nozzle structure of the invention comprises a cleansing water guide rib 3630 having a guide hole 3620 fluid-communicatively formed in a straight line inside the guide groove 3610. The guide hole 3620 guides the cleansing water discharged with a pressure such in a way as to stimulate an anus.

The procedures of using the spray nozzle structure will be described below.

First, when a constipated user is seated on the bidet and pushes the enema button of the controller in order to relieve himself or herself, the operator is rotated according to the control of the controller such that the three-directional nozzle 3500 is placed in a position to be able to carry out the enema function. At this state, as described above in conjunction with the embodiments, the waterway converter is rotated in order for the enema drain hole to be fluid-communicated with the enema moving hole 3513 of the cleansing water moving pipe 3510. Thereafter, the cleansing water stored in the water container of the bidet body is supplied according to the control of the controller In addition, when the cleansing water is introduced into the enema spray hole 3523 of the spray cap 3520 through the enema moving hole 3513 of the cleansing water moving pipe 3510, part of the cleansing water passing through the discharge hole 3524 is introduced into the inside of the guide groove 3610 of the guide rib 3630, thereby preventing turbulence of the cleansing water. The discharge hole 3524 is fluid-communicatively formed therein so as to have a diameter less than that of the enema spray hole 3523.

On the other hand, part of the cleansing water passed through the discharge hole 3524 is sprayed straight with a high pressure through the guide hole 3620 of the cleansing water guide rib 3600 by means of the pressure of the cleansing water. The guide hole 3620 of the cleansing water guide rib 3600 is fluid-communicated so as to have the same area as the discharge hole 3524.

At this time, the cleansing water does not generate turbulence and thus bubbles so that it can stimulate smoothly an anus and also be introduced into the inside of the rectum, thereby performing the enema function for relief.

INDUSTRIAL APPLICABILITY

As described above, a bidet having an enema function according to the present invention is constructed such in a manner that an anus-cleansing function, a bidet cleansing function, and an enema function are embodied in a single nozzle; or any one function is constituted on a spray tip projected from the separate spray nozzle body; or one or two functions among the anus-cleansing function, the bidet cleansing function and the enema function are embodied in two or three spray nozzles, which are projectably inserted in the lower central portion of the bidet body so as to be arranged horizontally adjacent to one anther; or one or two functions among the anus-cleansing function, the bidet cleansing function and the enema function are embodied in two or three spray nozzles, which are projectably inserted in the lower central portion of the bidet body so as to be arranged vertically adjacent to one anther.

Therefore, according to the present invention, a novel multi-functional bidet is provided, which can improve convenience of relief and sanitary concerns, called a core function of the bidet, and thus the user's health, without necessity of complicating the bidet structure or increasing the cost thereof owing to addition of other separate equipment.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:
1. A bidet having an enema function comprising:
   a) a support mounted on the bottom face of a bidet body;
   b) a controller mounted on a side of the bidet body and for selecting an anus-cleaning function, a bidet-cleaning function, and an enema function, and interrupting a selected function;
   c) an operator attached to an end portion of the support and for moving a three-directional nozzle correspondingly so as to perform the function selected by the controller,
   wherein the operator comprises: an operating motor affixed to one side of a support plate of the support such that a rotating axle is projected in a support hole of the support, the operating motor being clockwise or counterclockwise rotated in order for the three-directional nozzle of the support to be located correspondingly to the function selected in the controller; and a take-up member combined with the rotating axle of the operating motor and being rotated in the same manner of the operating motor; wherein an accommodating member affixed to the other side of the support plate receives the take-up member so as to prevent a leaf spring wound around the take-up member from escaping;
   d) a waterway converter for converting a waterway in order for a cleansing water to be supplied according to the function selected in the controller; and
   e) a spray-nozzle structure having the three-directional nozzle, wherein the three-directional nozzle is moved to a sliding space of the support and sprays the cleansing water passed through the waterway convert, thereby carrying out the function selected in the controller.

2. A bidet according to claim 1, wherein the support comprises:
   a) the sliding space where the three-directional nozzle slides thereon, the sliding space being mounted inclinedly on the bottom face of the bidet body;
   b) a guidance space provided at one end portion of the sliding space and for preventing escape of the three-directional nozzle sliding on the sliding space; and
   c) the support plate integrally provided and having the support hole fluid-communicatively formed vertically to the other end portion of the sliding space.

3. A bidet according to claim 1, wherein the waterway converter comprises:
   a) a stepping motor having the rotating axle projected therefrom, the rotating axle being clockwise or counterclockwise rotated so as to supply a cleaning water to the function selected in the controller;
   b) a connection member connected to the rotating axle of the stepping motor and being rotated in the same manner as the stepping motor;
   c) a fixed member mounted on one side of the stepping motor and receiving the connection member such that the end portion of the connection member is projected;
   d) a guidance member connected to a projected portion from the fixed member in order for the connection member to be freely rotated, the guidance member having a cleansing guide hole, a bidet guide hole, and an enema guide hole fluid-communicatively formed in the inner side thereof;
   e) a conversion member connected to an end portion of the connection member and closely contacted with the guidance member, the conversion member having a cleansing drain hole, a bidet drain hole, and an enema drain hole fluid-communicatively formed such that the direction of the cleaning water is fluid-communicated respectively with the cleansing guide hole, the bidet guide hole, and the enema guide hole of the guidance member according to the rotation of the stepping motor;
   f) a support member for receiving the guidance member mounted on the connection member and the conversion member in the inside of a body such that the outer circumferential face of the guidance member is tightly contacted with the inner circumferential face of the body, the body having an inlet hole projected on the outer circumferential face thereof for in-flowing the cleaning water, a moving hole being fluid-communicatively formed in a side face of the body so as to be fluid-communicated respectively with the cleansing drain hole, the bidet drain hole, and the enema drain hole; and g) a packing mounted on the outer circumferential face of the moving hole of the support member.

4. A bidet according to claim 3, wherein the guidance member is constructed in such a manner that the bidet guide hole is fluid-communicatively formed at the position perpendicularly crossing the center of the cleansing guide hole fluid-communicatively formed in the upper portion of the guidance member, and the enema guide hole is fluid-communicatively formed at the position facing the cleansing guide hole.

5. A bidet according to claim 3, wherein the conversion member is constructed in such a manner that the cleansing drain hole and the enema drain hole are fluid-communicatively formed between the cleansing guide hole and the enema guide hole, and the bidet drain hole is fluid-communicatively formed between the bidet guide hole and the enema guide hole.

6. A bidet according to claim 3, wherein the three-directional nozzle comprises:

a cleansing water moving pipe connected to an end portion of the support member so as to receiving the packing of the waterway converter, the cleansing water moving pipe having a cleansing moving hole, a bidet moving hole, and an enema moving hole fluid-communicatively formed so as to lie in the same line as the cleansing guide hole, the bidet guide hole, and the enema guide hole; and a spraying cap connected to an end portion of the cleansing water moving pipe and having a cleansing spraying hole, a bidet spraying hole, and an enema spraying hole fluid-communicatively formed so as to be fluid-communicated with the cleansing moving hole, the bidet moving hole, and the enema moving hole.

* * * * *